United States Patent
Parmer

(10) Patent No.: US 10,980,596 B2
(45) Date of Patent: Apr. 20, 2021

(54) VAGINAL REMODELING DEVICE AND METHODS

(71) Applicant: VIVEVE, INC., Sunnyvale, CA (US)

(72) Inventor: Jonathan B. Parmer, Woodside, CA (US)

(73) Assignee: Viveve, Inc., Englewood, CO (US)

( * ) Notice: Subject to any disclaimer, the term of this patent is extended or adjusted under 35 U.S.C. 154(b) by 370 days.

(21) Appl. No.: 14/629,186

(22) Filed: Feb. 23, 2015

(65) Prior Publication Data

US 2015/0327926 A1 Nov. 19, 2015

Related U.S. Application Data

(63) Continuation of application No. 11/704,067, filed on Feb. 7, 2007, now Pat. No. 8,961,511.

(Continued)

(51) Int. Cl.
*A61B 18/14* (2006.01)
*A61B 18/18* (2006.01)
(Continued)

(52) U.S. Cl.
CPC .......... *A61B 18/1485* (2013.01); *A61B 18/18* (2013.01); *A61N 7/022* (2013.01);
(Continued)

(58) Field of Classification Search
CPC .. A61B 2018/0016; A61B 2018/00559; A61B 2018/147
See application file for complete search history.

(56) References Cited

U.S. PATENT DOCUMENTS 2,811,969 A 11/1957 Shubert
3,403,684 A * 10/1968 Stiebel .................. A61N 1/372
607/72
(Continued)

FOREIGN PATENT DOCUMENTS

CN 2223112 Y 3/1996
CN 1241917 A 1/2000
(Continued)

OTHER PUBLICATIONS

Alinsod Institute for Aesthetic Vaginal Surgery; About Dr. Red Alinsod; 1 pg.; retrieved Feb. 21, 2017 from the internet at: http:/www.vaginalrejuvenationtraining.org/about.shtml.
(Continued)

*Primary Examiner* — Ronald Hupczey, Jr.
(74) *Attorney, Agent, or Firm* — Venable LLP; Michele V. Frank

(57) ABSTRACT

This invention relates generally to apparatus and methods for tightening tissue of the female genitalia by heating targeted connective tissue with radiant energy, while cooling the mucosal epithelial surface over the target tissue to protect it from the heat. Embodiments include a treatment tip that comprises both an energy delivery element and a cooling mechanism. As the treatment tip contacts the epithelial mucosa, the tip cools the mucosa by contact, and delivers energy through the epithelium to the underlying tissue, thereby creating a reverse thermal gradient. The effect of the applied heat is to remodel genital tissue by tightening it. Such remodeling may include a tighter vagina and a tighter introitus. The tightening may be a consequence of thermal denaturation of collagen as well as a longer term healing response in the tissue that includes an increased deposition of collagen.

58 Claims, 9 Drawing Sheets

Related U.S. Application Data

(60) Provisional application No. 60/743,247, filed on Feb. 7, 2006.

(51) Int. Cl.
*A61B 18/12* (2006.01)
*A61B 18/00* (2006.01)
*A61N 7/02* (2006.01)

(52) U.S. Cl.
CPC . *A61B 18/1206* (2013.01); *A61B 2018/00023* (2013.01); *A61B 2018/00559* (2013.01); *A61B 2018/00702* (2013.01); *A61B 2018/00791* (2013.01); *A61B 2018/00875* (2013.01)

(56) References Cited

U.S. PATENT DOCUMENTS

| | | |
|---|---|---|
| 3,595,217 A | 7/1971 | Rheinfrank |
| 3,741,211 A | 6/1973 | Vreeland |
| 3,995,629 A | 12/1976 | Patel |
| 4,309,989 A | 1/1982 | Fahim |
| 4,326,529 A | 4/1982 | Doss et al. |
| 4,381,007 A | 4/1983 | Doss |
| 4,454,764 A | 6/1984 | Sorenson |
| 4,785,807 A | 11/1988 | Blanch |
| 4,785,828 A | 11/1988 | Maurer |
| 4,881,526 A * | 11/1989 | Johnson ............... A61H 19/44 601/15 |
| 4,892,520 A | 1/1990 | Gilbaugh |
| 4,907,589 A | 3/1990 | Cosman |
| 4,920,978 A | 5/1990 | Colvin |
| 4,976,709 A | 12/1990 | Sand |
| 4,989,614 A | 2/1991 | Dejter, Jr. et al. |
| 5,010,895 A | 4/1991 | Maurer et al. |
| 5,046,511 A | 9/1991 | Maurer et al. |
| 5,143,063 A | 9/1992 | Fellner |
| 5,160,334 A | 11/1992 | Billings et al. |
| 5,230,349 A | 7/1993 | Langberg |
| 5,242,440 A | 9/1993 | Shippert |
| 5,301,692 A | 4/1994 | Knowlton |
| 5,330,469 A | 7/1994 | Fleenor |
| 5,334,193 A | 8/1994 | Nardella |
| 5,348,554 A | 9/1994 | Imran et al. |
| 5,403,311 A | 4/1995 | Abele et al. |
| 5,409,453 A | 4/1995 | Lundquist et al. |
| 5,443,470 A | 8/1995 | Stern et al. |
| 5,449,374 A | 9/1995 | Dunn et al. |
| 5,450,293 A | 9/1995 | Hoffman |
| 5,458,596 A | 10/1995 | Lax et al. |
| 5,469,857 A | 11/1995 | Laurent et al. |
| 5,569,242 A | 10/1996 | Lax et al. |
| 5,605,539 A * | 2/1997 | Buelna ............... A61B 18/1482 604/21 |
| 5,660,836 A | 8/1997 | Knowlton |
| 5,673,695 A | 10/1997 | McGee et al. |
| 5,755,753 A | 5/1998 | Knowlton |
| 5,765,567 A | 6/1998 | Knowlton |
| 5,807,392 A * | 9/1998 | Eggers ............... A61B 18/082 219/230 |
| 5,814,040 A | 9/1998 | Nelson et al. |
| 5,824,076 A | 10/1998 | Knowlton |
| 5,836,990 A | 11/1998 | Li |
| 5,871,524 A | 2/1999 | Knowlton |
| 5,893,849 A * | 4/1999 | Weaver ............... A61B 18/1402 606/39 |
| 5,919,219 A | 7/1999 | Knowlton |
| 5,937,863 A | 8/1999 | Knowlton |
| 5,947,891 A | 9/1999 | Morrison |
| 5,948,011 A | 9/1999 | Knowlton |
| 5,951,550 A | 9/1999 | Shirley et al. |
| 5,954,717 A | 9/1999 | Behl et al. |
| 5,957,922 A * | 9/1999 | Imran ............... A61B 18/1492 606/41 |
| 5,986,446 A | 11/1999 | Williamson |
| 6,002,968 A | 12/1999 | Edwards |
| 6,024,743 A | 2/2000 | Edwards |
| 6,035,238 A | 3/2000 | Ingle et al. |
| 6,044,847 A | 4/2000 | Carter et al. |
| 6,081,749 A | 6/2000 | Ingle et al. |
| 6,091,995 A | 7/2000 | Ingle et al. |
| 6,139,569 A | 10/2000 | Ingle et al. |
| 6,156,060 A | 12/2000 | Roy et al. |
| 6,169,914 B1 | 1/2001 | Hovland et al. |
| 6,216,704 B1 | 4/2001 | Ingle et al. |
| 6,236,891 B1 | 5/2001 | Ingle et al. |
| 6,241,753 B1 | 6/2001 | Knowlton |
| 6,277,116 B1 | 8/2001 | Utley et al. |
| 6,283,987 B1 * | 9/2001 | Laird ............... A61B 18/1485 606/40 |
| 6,292,700 B1 | 9/2001 | Morrison et al. |
| 6,311,090 B1 | 10/2001 | Knowlton |
| 6,322,584 B2 | 11/2001 | Ingle et al. |
| 6,350,276 B1 | 2/2002 | Knowlton |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,416,504 B2 | 7/2002 | Mosel et al. |
| 6,418,930 B1 | 7/2002 | Fowler |
| 6,425,912 B1 | 7/2002 | Knowlton |
| 6,427,089 B1 | 7/2002 | Knowlton |
| 6,430,446 B1 | 8/2002 | Knowlton |
| 6,432,105 B1 | 8/2002 | Ellman et al. |
| 6,438,424 B1 | 8/2002 | Knowlton |
| 6,453,202 B1 | 9/2002 | Knowlton |
| 6,461,332 B1 | 10/2002 | Mosel et al. |
| 6,461,378 B1 | 10/2002 | Knowlton |
| 6,463,331 B1 | 10/2002 | Edwards |
| 6,470,216 B1 | 10/2002 | Knowlton |
| 6,478,791 B1 | 11/2002 | Carter et al. |
| 6,480,746 B1 | 11/2002 | Ingle et al. |
| 6,482,204 B1 | 11/2002 | Lax et al. |
| 6,494,882 B1 | 12/2002 | Lebouitz et al. |
| 6,533,780 B1 | 3/2003 | Laird et al. |
| 6,546,934 B1 | 4/2003 | Ingle et al. |
| 6,558,381 B2 | 5/2003 | Ingle |
| 6,569,160 B1 | 5/2003 | Goldin |
| 6,572,639 B1 | 6/2003 | Ingle et al. |
| 6,579,266 B2 | 6/2003 | Mosel et al. |
| 6,587,731 B1 | 7/2003 | Ingle et al. |
| 6,607,525 B2 | 8/2003 | Franco |
| 6,629,535 B2 | 10/2003 | Ingle et al. |
| 6,629,974 B2 | 10/2003 | Penny et al. |
| 6,679,875 B2 | 1/2004 | Honda et al. |
| 6,681,771 B2 | 1/2004 | Durette |
| 6,685,623 B2 | 2/2004 | Presthus et al. |
| 6,692,490 B1 | 2/2004 | Edwards |
| 6,741,895 B1 * | 5/2004 | Gafni ............... A61B 5/4337 600/38 |
| 6,743,165 B2 | 6/2004 | Mosel et al. |
| 6,749,624 B2 | 6/2004 | Knowlton |
| 6,751,507 B2 | 6/2004 | Morrison et al. |
| 6,772,013 B1 | 8/2004 | Ingle et al. |
| 6,776,779 B1 | 8/2004 | Roy et al. |
| 6,830,052 B2 | 12/2004 | Carter et al. |
| 6,836,688 B2 | 12/2004 | Ingle et al. |
| 6,840,954 B2 | 1/2005 | Dietz et al. |
| 6,852,110 B2 | 2/2005 | Roy et al. |
| 6,875,209 B2 | 4/2005 | Zvuloni et al. |
| 6,879,858 B1 | 4/2005 | Adams |
| 6,882,885 B2 | 4/2005 | Levy et al. |
| 6,889,090 B2 | 5/2005 | Kreindel |
| 6,976,492 B2 | 12/2005 | Ingle et al. |
| 7,004,942 B2 | 2/2006 | Laird et al. |
| 7,022,121 B2 | 4/2006 | Stern et al. |
| 7,104,990 B2 * | 9/2006 | Jenkins ............... A61B 18/1492 606/41 |
| 7,141,049 B2 | 11/2006 | Stern et al. |
| 7,167,757 B2 | 1/2007 | Ingle et al. |
| 7,238,183 B2 | 7/2007 | Kreindel |

(56) References Cited

U.S. PATENT DOCUMENTS

| | | |
|---|---|---|
| 7,294,127 B2 | 11/2007 | Leung et al. |
| 7,315,762 B2 | 1/2008 | Mosher et al. |
| 7,473,251 B2 | 1/2009 | Knowlton et al. |
| 7,479,140 B2 | 1/2009 | Ellman et al. |
| 7,536,225 B2 | 5/2009 | Spraker et al. |
| 7,630,774 B2 | 12/2009 | Karni et al. |
| 7,792,589 B2 | 9/2010 | Levy, Jr. et al. |
| 7,837,682 B2 | 11/2010 | Ostrovsky et al. |
| 7,850,683 B2 | 12/2010 | Elkins et al. |
| 7,998,137 B2 | 8/2011 | Elkins et al. |
| 8,206,385 B2 * | 6/2012 | Stangenes ............ A61B 5/0422 606/32 |
| 8,262,715 B2 | 9/2012 | Wong, Jr. et al. |
| 8,317,782 B1 | 11/2012 | Ellman et al. |
| 8,409,185 B2 | 4/2013 | Burger et al. |
| 8,603,084 B2 | 12/2013 | Fish et al. |
| 8,702,691 B2 | 4/2014 | Weber et al. |
| 8,961,511 B2 | 2/2015 | Parmer |
| 9,028,484 B2 | 5/2015 | Craig |
| 9,149,322 B2 | 10/2015 | Knowlton |
| 9,271,785 B2 | 3/2016 | Parmer et al. |
| 2002/0032441 A1 | 3/2002 | Ingle et al. |
| 2002/0049483 A1 | 4/2002 | Knowlton |
| 2002/0062142 A1 | 5/2002 | Knowlton |
| 2002/0120260 A1 | 8/2002 | Morris et al. |
| 2002/0151887 A1 | 10/2002 | Stern et al. |
| 2002/0156471 A1 | 10/2002 | Stern et al. |
| 2002/0183735 A1 | 12/2002 | Edwards et al. |
| 2003/0028180 A1 | 2/2003 | Franco |
| 2003/0097162 A1 | 5/2003 | Kreindel |
| 2003/0120326 A1 | 6/2003 | Dietz et al. |
| 2003/0130575 A1 | 7/2003 | Desai |
| 2003/0139740 A1 | 7/2003 | Kreindel |
| 2003/0139790 A1 | 7/2003 | Ingle et al. |
| 2003/0144576 A1 | 7/2003 | Presthus et al. |
| 2003/0178032 A1 | 9/2003 | Ingle et al. |
| 2003/0195593 A1 | 10/2003 | Ingle et al. |
| 2003/0195604 A1 | 10/2003 | Ingle et al. |
| 2003/0199866 A1 | 10/2003 | Stern et al. |
| 2003/0212393 A1 | 11/2003 | Knowlton et al. |
| 2003/0212395 A1 | 11/2003 | Woloszko et al. |
| 2003/0216728 A1 | 11/2003 | Stern et al. |
| 2003/0216729 A1 | 11/2003 | Marchitto et al. |
| 2003/0220635 A1 | 11/2003 | Knowlton et al. |
| 2003/0236487 A1 | 12/2003 | Knowlton |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0030332 A1 | 2/2004 | Knowlton et al. |
| 2004/0034346 A1 | 2/2004 | Stern et al. |
| 2004/0034400 A1 | 2/2004 | Ingle et al. |
| 2004/0049251 A1 | 3/2004 | Knowlton |
| 2004/0102824 A1 | 5/2004 | Sharkey et al. |
| 2004/0111087 A1 | 6/2004 | Stern et al. |
| 2004/0111136 A1 | 6/2004 | Sharkey et al. |
| 2004/0111137 A1 | 6/2004 | Shankey et al. |
| 2004/0127895 A1 | 7/2004 | Flock et al. |
| 2004/0162554 A1 | 8/2004 | Lee et al. |
| 2004/0172291 A1 | 9/2004 | Knowlton |
| 2004/0186535 A1 | 9/2004 | Knowlton |
| 2004/0193238 A1 | 9/2004 | Mosher et al. |
| 2004/0206365 A1 | 10/2004 | Knowlton |
| 2004/0210214 A1 | 10/2004 | Knowlton |
| 2004/0210282 A1 | 10/2004 | Flock et al. |
| 2004/0236177 A1 | 11/2004 | Matlock |
| 2004/0236393 A1 | 11/2004 | Ingle et al. |
| 2004/0249425 A1 * | 12/2004 | Roy ...................... A61N 1/403 607/99 |
| 2004/0260368 A1 | 12/2004 | Ingle et al. |
| 2004/0267336 A1 | 12/2004 | Morrison et al. |
| 2005/0154433 A1 | 7/2005 | Levy, Jr. et al. |
| 2005/0171582 A1 | 8/2005 | Matlock |
| 2005/0171583 A1 | 8/2005 | Mosher et al. |
| 2005/0187599 A1 | 8/2005 | Sharkey et al. |
| 2005/0203399 A1 | 9/2005 | Vaezy et al. |
| 2005/0288544 A9 | 12/2005 | Matlock |
| 2005/0288680 A1 | 12/2005 | Ingle et al. |
| 2006/0025837 A1 | 2/2006 | Stern et al. |
| 2006/0047331 A1 | 3/2006 | Lax et al. |
| 2006/0167533 A1 | 7/2006 | Spraker et al. |
| 2006/0224090 A1 | 10/2006 | Ostrovsky et al. |
| 2006/0241530 A1 | 10/2006 | Ostrovsky et al. |
| 2007/0078502 A1 | 4/2007 | Weber et al. |
| 2007/0083247 A1 | 4/2007 | Wyeth et al. |
| 2007/0088413 A1 | 4/2007 | Weber et al. |
| 2007/0093807 A1 | 4/2007 | Baxter et al. |
| 2007/0106349 A1 | 5/2007 | Karni et al. |
| 2007/0219602 A1 | 9/2007 | Ostrovsky et al. |
| 2007/0233191 A1 | 10/2007 | Parmer |
| 2008/0200969 A1 | 8/2008 | Weber |
| 2009/0076496 A1 | 3/2009 | Azure |
| 2009/0149928 A1 | 6/2009 | Relin |
| 2010/0049186 A1 | 2/2010 | Ingle et al. |
| 2011/0096802 A1 | 4/2011 | Boutoussov et al. |
| 2011/0178584 A1 | 7/2011 | Parmer et al. |
| 2011/0202108 A1 | 8/2011 | Gross |
| 2012/0016239 A1 | 1/2012 | Barthe et al. |
| 2012/0046547 A1 | 2/2012 | Barthe et al. |
| 2012/0136407 A1 | 5/2012 | Presthus et al. |
| 2013/0096431 A1 | 4/2013 | Vaezy et al. |
| 2013/0245728 A1 | 9/2013 | Galen et al. |
| 2015/0165241 A1 | 6/2015 | Burdette |
| 2015/0202467 A1 | 7/2015 | Diederich |
| 2015/0327926 A1 | 11/2015 | Parmer |
| 2015/0366747 A1 | 12/2015 | Lei |
| 2016/0135876 A1 | 5/2016 | Parmer et al. |
| 2016/0183996 A1 | 6/2016 | Burger et al. |
| 2016/0296278 A1 | 10/2016 | Galen et al. |

FOREIGN PATENT DOCUMENTS

| | | |
|---|---|---|
| CN | 2454769 Y | 10/2001 |
| CN | 1778414 A | 5/2006 |
| CN | 1868396 A | 11/2006 |
| CN | 2885157 Y | 4/2007 |
| CN | 2897183 Y | 5/2007 |
| CN | 101229078 A | 7/2008 |
| CN | 101273874 A | 10/2008 |
| CN | 201286935 Y | 8/2009 |
| CN | 101810505 A | 8/2010 |
| CN | 202724094 U | 2/2013 |
| CN | 202751492 U | 2/2013 |
| CN | 202859437 U | 4/2013 |
| CN | 10330961 A | 9/2013 |
| DE | 202014100400 U1 | 2/2014 |
| EP | 0253677 B1 | 9/1993 |
| EP | 2856986 A1 | 4/2015 |
| JP | H05-269144 A | 10/1993 |
| JP | H09-122141 A | 5/1997 |
| JP | H09-140802 A | 6/1997 |
| JP | H11-504828 A | 5/1999 |
| JP | 2000-507118 A | 6/2000 |
| JP | 2001514921 A | 9/2001 |
| JP | 2002-238919 A | 8/2002 |
| JP | 2003503118 | 1/2003 |
| JP | 2005198896 A | 7/2005 |
| JP | 2005318953 A | 11/2005 |
| JP | 2006-187668 A | 7/2006 |
| JP | 2006-517422 A | 7/2006 |
| KR | 20100087521 A | 8/2010 |
| KR | 20120010737 A | 2/2012 |
| RU | 2125846 C1 | 1/1997 |
| RU | 2207823 C2 | 7/2003 |
| RU | 2217186 C1 | 11/2003 |
| RU | 2291673 C1 | 1/2007 |
| TW | 200305649 A | 11/2003 |
| TW | 200716624 A | 5/2007 |
| TW | 200724083 A | 7/2007 |
| TW | I288637 B | 10/2007 |
| TW | 200831152 A | 8/2008 |
| TW | 200938247 A | 9/2009 |
| TW | I314449 B | 9/2009 |
| WO | WO94/26345 A1 | 11/1994 |
| WO | WO95/10981 A1 | 4/1995 |

(56) References Cited

FOREIGN PATENT DOCUMENTS

| WO | WO96/22739 A1 | 8/1996 |
|---|---|---|
| WO | 96034568 A1 | 11/1996 |
| WO | 97029701 A1 | 8/1997 |
| WO | WO97/34534 A1 | 9/1997 |
| WO | WO98/19613 A1 | 5/1998 |
| WO | WO99/08614 A1 | 2/1999 |
| WO | WO99/53853 A1 | 10/1999 |
| WO | 2000/010475 A1 | 3/2000 |
| WO | 2001000269 A1 | 1/2001 |
| WO | WO01/80723 A2 | 11/2001 |
| WO | WO02/07657 A1 | 1/2002 |
| WO | WO03/011158 A1 | 2/2003 |
| WO | WO03/053355 A2 | 7/2003 |
| WO | WO2005/063138 A1 | 7/2005 |
| WO | WO2006/033067 A2 | 3/2006 |
| WO | WO2006/034357 A2 | 3/2006 |
| WO | WO2006/103678 A2 | 10/2006 |
| WO | WO2006/105121 A2 | 10/2006 |
| WO | WO2000/153999 A1 | 12/2008 |
| WO | 2011034986 A2 | 3/2011 |
| WO | 2011/066445 A2 | 6/2011 |
| WO | 2014165242 A1 | 10/2014 |
| WO | 2016004295 A1 | 1/2016 |

OTHER PUBLICATIONS

Dmochowski et al., Transvaginal Radio Frequency Treatment of the Endopelvic Fascia: A Prospective Evaluation for the Treatment of Genuine Stress Urinary Incontinence, 169(3), J. or Urology, pp. 1028-1032, Mar. 2003.

Dmochowski, Radiofrequency Bladder Neck Suspension for the Treatment of Genuine Stress Urinary Incontinence, Current Urology Reports, 3(5), pp. 378-381, Oct. 2002.

Laser Vaginal Rejuvenation Center of Los Angeles, Laser Vaginal Rejuvenation for the Enhancement of Sexual Gratification: About Dr. Matlock, 8 pgs., © 2000, retrieved Mar. 30, 2017 at: https://web.archive.org/web/20001002113647/http:/www.drmatlock.com/laserVR.htm.

Lenihan, Jr., Comparison of the Quality of Life After Nonsurgical Radiofrequency Energy Tissue Micro-Remodeling in Premenopausal and Postmenopausal Women With Moderate-to-Severe Stress Urinary Incontinence, Am. J. of Obstetrics and Gynecology, 192(6), pp. 1995-2001, Jun. 2005.

Ollivier, Designer Vaginas, Salon, 4 pgs., Nov. 14, 2000, retrieved Mar. 30, 2017 at http://www.salon.com/2000/11/14/vagina_3/.

Reid et al., Flashlamp-Excited Dye Laser Therapy of Idiopathic Vulvodynia is Safe and Efficacious, Am. J. Obstet. Gynecol., 172(6), pp. 1684-1701, Jun. 1995.

Ross et al., A Prospective Multisite Study of Radiofrequency Bipolar Energy for Treatment of Genuine Stress Incontinence, J. of the American Association of Gynecologic Laparoscopists, 9 (4), pp. 493-499, Nov. 2002.

Sotomayor et al., Twelve-Month Results of Nonsurgical Radiofrequency Energy Micro-Remodeling for Stress Incontinence, 16 Int. Urogynecol. J., 16(3), pp. 192-196, May-Jun. 2004.

Thermigen, LLC; Ask Your Doctor How Controlled Radiofrequency Might Benefit You, THERMIva (advertisement); document No. MA-PA-TVA2 Rev A; 1 page; this web address was available to applicant(s) at least as of Feb. 23, 2017.

Thermigen, LLC; Everyone Is Talking About the Benefits of Temperature Controlled Radiofrequency, THERMIva (advertisement); document No. MC-TVA-03 Rev B; 2 pgs.; this web address was available to applicant(s) at least as of Feb. 23, 2017.

Thermigen, LLC; Now Offering . . . THERMIva (physician advertisement); document No. MA-PA-TVA1 Rev A; 1 page; this web address was available to applicant(s) at least as of Feb. 23, 2017.

Thermigen, LLC; The Science of Heat, The Beauty of Control. THERMIva (product information); document No. MA-PY-TVA-1 Rev A; 1 page; this web address was available to applicant(s) at least as of Feb. 23, 2017.

Thermigen, LLC; THERMIva Non-Surgical Vulvovaginal Rejuvination (product advertisement);1 page; this web address was available to applicant(s) at least as of Feb. 23, 2017.

Thermigen, LLC; THERMIva: Minimally-Invasive Electrocoagulation (product information); document No. MC-TVA 04 Rev B; 1 pg.; this web address was available to applicant(s) at least as of Feb. 23, 2017.

Zelickson et al., Histological and Ultrastructural Evaluation of the Effects of a Radiofrequency-Based Nonablative Dermal Remodeling Device: A Pilot Study, Arch Dermatol, 140(2), pp. 204-209, Feb. 2004.

Alinsod; What are the differences between thermiva radiofrequency and femilift/monalisa/intimalase lasers for use in aesthetic vulvovaginal therapies; 12 pages; retrived from the internet at (https://www.linkedin.com/pulse/what-differences-between-thermiva-radiofrequency-use-alinsod-m-d-/?published=u) on Jan. 16, 2017.

Taber's Cyclopedic Medical Dictionary; Ablation (definition); F. A. Davies Company; 3 pages; (year of pub. sufficiently earlier than effective US filing date and any foreign priority date) 2005.

ThermiVa: Doctors are Weighing in on ThermiVa; 4 pages; retrieved from the internet (http://thermiva.org/doctors-are-wieghing-in.) on Aug. 20, 2015.

Webster's Third New International Dictionary; Over (definition); Merriam-Webster, Inc.; 3 pages; (year of pub. sufficiently earlier than effective US filing date and any foreign priority date) 2002.

Beattie et al.; UVA1 phototherapy for genital lichen sclerosus; Clinical and Experimental Dermatology; 31(3); pp. 343-347; May 1, 2006.

Bieber eet al.; The Gynecologic resectoscope; Chapter # The tissue effects of radiofrequency electrosurgical currents; Blackwell Science, Inc.; pp. 27-46; (year of pub. sufficiently earlier than effective US filing date and any foreign priority date); 1995.

Kreuter et al.; Low-dose ultraviolet A1 phototherapy for extragenital lichen sclerosus: results of preliminary study; Journal of the American Academy of Dermatology; 46(2); pp. 251-255; Feb. 2002.

Peterson et al.; Successful carbon dioxide laser therapy for refractory anogenital lichen sclerosus; Dermatologic Surgery; 30(8); pp. 1148-1151; Aug. 1, 2004.

Smith et al.; Vulvar lichen sclerosus; American Journal of Clinical Dermatology; 5(2); pp. 105-125; (Author Manuscript) Apr. 1, 2004.

Office Action issued in related Indian Patent Application No. 2321/DELNP/2012, dated Oct. 26, 2018.

Office Action issued in related U.S. Appl. No. 14/629,186, dated Jul. 18, 2019.

Office Action issued in related Chinese Patent Application No. 201610223768.4 dated Feb. 11, 2019.

Office Action issued in related U.S. Appl. No. 15/268,398, dated Jun. 27, 2019.

Office Action issued in related Japanese Patent Application o. 2017-3686, dated Feb. 27, 2019.

Office Action issued in related U.S. Appl. No. 15/188,948, dated May 28, 2019.

Extended European Search Report issued in related European Patent Application No. 18168440.8 dated Jun. 22, 2018.

Office Action issued in related Korean Patent Application No. 10-2017-7015034, dated Oct. 19, 2018.

Office Action issued in related Brazilian Patent Application No. 1120120060597 dated Jul. 23, 2019.

International Search Report and Written Opinion issued in related International Patent Application No. PCT/US2018/016266 dated Sep. 8, 2018.

Office Action issued in related Korean Patent Application No. 10-2019-7105773 dated Jul. 22, 2019.

Liberate (International) VI-17-01 Evaluatyion of the Safety and Efficacy of the Viveve Geneveve Treatment for Stress Urinary Incontinence, Clinical Protocol, pp. 1-49 (Apr. 9, 2018).

International Search Report issued in related Intentional Patent Application No. PCT/US2010/049045 dated May 9, 2011.

Written Opinion of the International Searching Authority issued in related Intentional Patent Application No. PCT/US2010/049045, dated May 9, 2011.

Chinese Search Report issued in related Chinese Patent Application No. 201220099603.8, dated Apr. 12, 2013.

(56) References Cited

OTHER PUBLICATIONS

Chinese Search Report issued in related Chinese Patent Application No. 201220099605.7, dated Apr. 12, 2013.
Chinese Search Report issued in related Chinese Patent Application No. 201220099618.4, dated Apr. 12, 2013.
Chinese Search Report issued in related Chinese Patent Application No. 201220099620.1, dated Apr. 12, 2013.
Chinese Search Report issued in related Chinese Patent Application No. 201220099634.3, dated Apr. 12, 2013.
Chinese Search Report issued in related Chinese Patent Application No. 201220099648.5, dated Apr. 12, 2013.
International Search Report issued in related Intentional Patent Application No. PCT/US2013/032066, dated Jun. 6, 2013.
Written Opinion of the International Searching Authority issued in related Intentional PatentApplication No. PCT/U52013/032066, dated Jun. 6, 2013.
Office Action issued in related U.S. Appl. No. 12/884,108, dated Oct. 9, 2013.
Office Action issued in related U.S. Appl. No. 12/884,108, dated Feb. 6, 2014.
Office Action issued in related Chinese Patent Application No. 201210069909.3, dated Aug. 26, 2014.
Office Action issued in related U.S. Appl. No. 12/884,108, dated Aug. 27, 2014.
Office Action issued in related Chinese Patent Application No. 201210069910.6, dated Sep. 4, 2014.
Office Action issued in related Chinese Patent Application No. 201210069906,X, dated Sep. 4, 2014.
Office Action issued in U.S. Appl. No. 12/884,108, dated Mar. 17, 2015.
Extended European Search Report issued in related European Patent Application No. EP13760612.5, dated Mar. 24, 2015.
Office Action issued in related Chinese Patent Application No. 201210069906.X, dated Mar. 24, 2015.
Office Action issued in related Russian Patent Application No. RU 2014141309, dated Jan. 10, 2017.
Bergman et al., "Role of the Q-tip Test in Evaluating Stress Urinary Incontinence" The Journal of reproductive medicine, 32(4):273-5 (1987).
Weigel et al., "The Female Sexual Function Index (FSFI): Cross-Validation and Development of Clinical Cutoff Scores" Journal of Sex & Marital Therapy, 31:1-20 (2005).
Verrico et al., "Expression of the collagen-related heat shock protein HSP47 in fibroblasts treated with hyperthermia or photodynamic therapy" British Journal of Cancer (76(6):719-724 (1997).
Uebersax et al., "Short Forms to Assess Life Quality and Symptom Distress for Urinary Incontinence in Women: The Incontinence Impact Questionnaire and the Urogenital Distress Inventory" Neurourology and Urodynamics 14: 131-139 (1995).
Harvey et al., "The Incontinence Impact Questionnaire and the Urogenital Distress Inventory: A revisit of their validity in women without a urodynamic diagnosis" Am J Obstet Gynecol, 185:25-31 (2001).
Tähtinen et al., "Long-term Impact of Mode of Delivery on Stress Urinary Incontinence and Urgency Urinary Incontinence: A Systematic Review and Meta-analysis" European Urology 7 0 : 1 4 8-1 5 8 (2016).
Shumaker et al., "Health-Related Quality of Life Measures for Women with Urinary Incontinence: the Incontinence Impact Questionnaire and the Urogenital Distress Inventory" Quality of Life Research, 3, pp. 291-306 (1994).
Sekiguchi et al., "Laxity of the Vaginal Introitus After Childbirth: Nonsurgical Outpatient Procedure for Vaginal Tissue Restoration and Improved Sexual Satisfaction Using Low-Energy Radiofrequency Thermal Therapy" Journal of Women's Health, 22(9):775-781 (2013).
Sajjadi et al., "Expression of heat shock proteins 70 and 47 in tissues following short-pulse laser irradiation: Assessment of thermal damage and healing" Medical Engineering & Physics, 35(10):1-9 (Apr. 2013).
Rosen et al., "The Female Sexual Function Index (FSFI): A Multidimensional Self-Report Instrument for the Assessment of Female Sexual Function" Journal of Sex & Marital Therapy, 26:191-208 (2000).
Patrick et al., "Quality of Life of Women With Urinary Incontinence: Further Development of the Incontinence Quality of Life Instrument (I-QOL)" Urology 53: 71-76 (1999).
Millheiser et al., "Radiofrequency Treatment of Vaginal Laxity after Vaginal Delivery: Nonsurgical Vaginal Tightening" J Sex Med, 7:3088-3095 (2010).
Krhut et al., "ICS Teaching Module: Pad Weight Testing in the Evaluation of Urinary Incontinence" International Continence Society (Unknown).
Kawasaki et al., "Deletion of the Collagen-specific Molecular Chaperone Hsp47 Causes Endoplasmic Reticulum Stress-mediated Apoptosis of Hepatic Stellate Cells*" The Journal of Biological Chemistry, 290 (6):3639-3646 (2015).
Urinary Incontinence in Women, Practice Bulletin, Clinical Management Guidelines for Obstetrician-Gynecologists, Obstetrics and Gynecology, 126(5):e66-e81 (2015).
Avery et al., "ICIQ: A Brief and Robust Measure for Evaluating the Symptoms and Impact of Urinary Incontinence" Neurourology and Urodynamics 23:322-330 (2004).
Macrene, Alexiades, MD, Ph.D., et al. "Randomized, Blinded, 3-Arm Clinical Trial Assessing Optimal Temperature and Duration for Treatment With Minimally Invasive Fractional Radiofrequency", American Society for Dermatologic Surgery, 2015, 41:623-632 (10 pages).
Dany Berube, Ph.D., et al., "A Predictive Model of Minimally Invasive Bipolar Fractional Radiofrequency Skin Treatment", Lasers in Surgery and Medicine, 2009, 41:473-478 (6 pages).
Femilift / Alma Surgical "Clinical Solutions for a Better Feminine Life", retrieved Sep. 16, 2015 from http://www.almasurgical.com/applications/femililift/ (8 pages).
IncontiLase/Gynecology/Fotona, retrieved Sep. 16, 2015 from http://www.fotona.com/en/treatments/1309/incontilase/ (3 pages).
Venn Healthcare Petite Lady, retrieved Sep. 19, 2015 from http://venthealthcare.com/petite-lady (4 pages).
Office Action issued in related Chinese Patent Application No. CN201610223768.4 dated Jun. 8, 2018.
Office Action issued in related Chinese Patent Application No. 201610244844.X, dated Dec. 12, 2017.
Notice of Dismissal of Amendment issued in related Korean Patent Application No. 10-2014-7029000 dated May 1, 2017.
Office Action issued in related Japanese Patent Application No. 2017-003686 dated Aug. 27, 2018.
Office Action issued in related Taiwanese Patent Application No. 106103270 dated Jul. 10, 2018.
Office Action issued in related Chinese Patent Application No. 201610244844, dated Feb. 26, 2019.
Office Action issued in related Taiwanese Patent Application No. 106103270, dated Apr. 10, 2019.
Office Action issued in related U.S. Appl. No. 15/188,948 dated Oct. 25, 2019.
Korean Office Action issued in related Korean Patent Application No. 10-2019-7034110 dated Feb. 18, 2020.
Office Action issued in related Brazilian Patent Application No. BR112014022866-3 dated Feb. 18, 2020.
International Search Report and Written Opinion issued in related International Patent Application No. PCT/US2018/033472 dated Oct. 31, 2018.
Office Action issued in related Canadian Patent Application No. 3,028,905 dated Oct. 15, 2019.
Office Action issued in related Taiwanese Patent Application No. 107138144 dated Oct. 1, 2019.
Australian Examination Report for corresponding AU Application No. 2016324168 dated Jun. 2, 2020.
Final Office Action for corresponding U.S. Appl. No. 15/188,948 dated Jul. 6, 2020.

* cited by examiner

VAGINAL REMODELING DEVICE AND METHODS

CROSS REFERENCE TO RELATED APPLICATIONS

This patent application is a continuation of U.S. patent application Ser. No. 11/704,067, filed Feb. 7, 2007, entitled "VAGINAL REMODELING DEVICE AND METHODS," which claims priority to U.S. Provisional Application No. 60/743,247, filed on Feb. 7, 2006, entitled "VAGINAL REJUVENATION TREATMENT DEVICE AND METHODS", each of which is herein incorporated by reference in its entirety

FIELD OF THE INVENTION

This invention relates generally to a method and apparatus for remodeling tissue of the vagina and vulva, such as by the application of radiant energy.

BACKGROUND

The vagina is made up of three layers, a mucosa of stratified squamous epithelial tissue, the submucosa or lamina propria containing vascularized connective tissue and a deeper muscularis, containing smooth muscle. Collagen molecules are produced by cells resident in the these tissues which synthesize three polypeptide chains that wrap around one another to form a triple helix. Collagen is a major type of fibrous protein that is a basic structural element of connective tissue, tendon, cartilage, and bone. Each of the collagen chains is approximately 1000 amino acid units in length, with glycine recurring regularly every third unit, and with proline and hydroxyproline recurring very frequently. Cross-linking occurs between the sides, not the ends, of collagen molecules and is coupled with the amino acid composition to give collagen its great strength. Collagen tissue tightening takes place in a direction parallel to an axis of collagen fibers.

The phenomenon of thermal contraction of collagen begins with a denaturation of the triple helix of the collagen molecule. Partial denaturation of collagen tissue results in a contraction of the collagen-rich spaces and provides a "tightening" effect on the overlaying tissue. Patents relevant to aspects of collagen denaturation and exploitation of this for medical or cosmetic purposes include U.S. Pat. No. 5,919,219 to Knowlton for "Method for Controlled Contraction of Collagen Tissue Using RF Energy" and U.S. Pat. No. 5,755,753 to Knowlton for "Method for Controlled Contraction of Collagen Tissue"; and U.S. Pat. No. 5,143,063 to Fellner for "Method of Removing Adipose Tissue".

Further patents and published patent applications include U.S. Pat. No. 6,350,276 to Knowlton for "Tissue Remodeling Apparatus Containing Cooling Fluid"; U.S. Pat. No. 6,387,380 to Knowlton for "Apparatus for Controlled Contraction of Collagen Tissue"; U.S. Pat. No. 6,425,912 to Knowlton for "Method and Apparatus for Modifying Skin Surface and Soft Tissue Structure"; U.S. Pat. No. 6,453,202 to Knowlton for "Apparatus for Tissue Remodeling"; U.S. Pub 2002/0049483 to Knowlton for "Fluid Delivery Apparatus"; U.S. Pub 2003/0212393 to Knowlton for "Handpiece with RD Electrode and Non-Volatile Memory"; U.S. Pub 2003/0236487 to Knowlton for "Method for Treatment of Tissue with Feedback"; and U.S. Pub 2004/0000316 to Knowlton for "Methods for Creating Tissue Effect Utilizing Electromagnetic Energy and a Reverse Thermal Gradient".

The vaginal tissue of women is stretched during vaginal child birth; at least some of the effects of the stretching are permanent and many women have long term medical consequences. Some consequences include physical problems, such as uterine prolapse, cystoceles, urethroceles, enteroceles, rectoceles, stress urinary incontinence, bowel movement problems, for which surgical options are available. Some consequences may include sexual aspects, as may follow from excessive loosening of the vagina and its opening, the introitus. Such loosening typically occurs with the first vaginal delivery, and the loosening tends to increase with subsequent vaginal deliveries. This effective of looseness in this region may include decreased pressure and friction during intercourse, and as a consequence, decreased sexual pleasure for women and their conjugal partners. Some surgical options can be exercised in an attempt to alleviate these problems, but surgical approaches can bring with them a risk of scarring that is entirely counterproductive with regard to the desired result. More generally, these surgical approaches are not highly popular because of the risks associated with an invasive procedure, in a sensitive area, especially when such procedures are considered medically optional.

There is a need for effective approaches to treating a loose vagina and introitus with a non-invasive procedure; accordingly, the object of the present invention to provide apparatus and method for corrective or restorative remodeling of the mucosal surfaces of the vagina, introitus, and vulva.

SUMMARY OF THE INVENTION

Embodiments of the invention include an apparatus for remodeling target tissues, including the lamina propria and the muscularis, underlying the mucosal epithelium of a female genital tissue. The apparatus comprises a hand piece and a treatment tip, the hand piece further supported a by comprehensive upstream electronic system. Embodiments of the treatment tip comprise a connector portion, which connects the tip to the hand piece, a midsection, typically narrowed, and a distal portion that comprises an energy delivery element. The treatment tip further comprises a housing that defines an internal space. The internal space accommodates a cooling system, with a lumen for conveying a refrigerating fluid, and nozzles, which are adapted to spray refrigerant on to the internal side of the energy delivery element thereby cooling it, such the cooled, in turn, cooling a genital mucosal epithelial surface on contact.

The types of energy delivery element may include a radiofrequency, microwave, or ultrasound delivery embodiments. Some particular embodiments include capacitively coupled RF electrodes, which may by monopolar or bipolar. Monopolar RF electrode-based embodiments may comprise a conductive pad to serve as a return electrode. Bipolar RF-based embodiments may include one or more pairs of electrodes. The electrodes may further comprise thermal sensors that provide feedback control based on local temperature, and may further comprise EEROM chips that identify the treatment tip type or convey configuration parameters of the electrode to the hand piece, or to the larger electronic system.

The energy delivery element and the treatment tip as a whole are adapted to make optimal contact with the genital epithelial surface, when contact and capacitive coupling is occurring between the tip and an epithelial contact site. By optimal contact is meant a contact that best allows a delivery of energy into the target tissue that is broadly uniform across the surface of the contact site, notably without significant distortion along the edges of the contact site. Non-uniform delivery of energy does not serve the remodeling process well, and further may risk damage to the mucosal epithelium. These adaptive configurations include a sidemounted configuration of the energy delivery element, the face of the energy delivery element being substantially parallel with respect to the linear axis of the treatment tip. Other adaptive configurations include a narrowed mid-section of the tip proximal to the distal portion. This configuration allows the energy delivery element at the distal portion of the tip to project outward or forward from its surrounding support structure, thereby allowing the contact between the energy delivery element and the mucosal epithelium to be more accurate, deliberate, and visible, and for the level of contacting pressure to be better controlled by the physician.

Further, the dimensions and configuration of the energy delivery element are adapted to the optimize contact, particularly with the vaginal wall. The width of the energy delivery element is between 0.75 and 1.25 cm. Such a width is sufficient to engage the curved wall of the vagina in a manner that is sufficiently flat and parallel that the quality of contact across the face of the energy delivery element is substantially equal, without increased pressure, closer contact, or distortion along the edges of the element. Such a close contact allows for a uniform delivery of energy into the underlying target tissue. In some embodiments, the face of the energy delivery element is radially curved (with respect to the longitudinal axis of the tip) within the width of the element so as to create an arc of up to 30 degrees. Such curvature is also adapted to make parallel contact with the vaginal wall. An element of about 1 cm width, per embodiments of the invention, requires about 10 contact sites to radially treat a 300 degree arc inside a vagina, thus a 30 degree arc provides for a good fit against the curve of the vaginal wall and thereby provides a uniform delivery of energy into the target tissue.

In typical embodiments, the length of the energy delivery element is about 1 to about 3 cm in length, in other embodiments it may be as long as about 4 cm. This is a length well adapted to treating the lower aspect of the vagina, wherein treatment by the method comprises contacting the vaginal epithelium in a region that extends from the introitus inward to a position about 3 to 4 cm inward from the introitus. In some embodiments of the invention, the method can by practiced with a single row of parallel contact sites immediately inside the introitus. In other embodiments, the method may include deeper rows, or rows that overlap an initial row, while keeping the contact sites within the lower portion of the vagina.

Embodiments of the invention include methods for remodeling a therapeutic zone of tissue within a target tissue of female genitalia. The target tissue lies immediately beneath the mucosal epithelium of genital tissues, and includes the lamina propria, a connective tissue that includes collagen in the extracellular space, and the muscularis, which includes smooth muscle. The target zone of embodiments of the invention does not include deeper tissue, such as endopelvic fascia.

The anatomical areas of the female genitalia treated by embodiment of the invention include the vulva and the vagina, and the introitus, the opening of the vagina. The vulva includes tissue radiating outward from the introitus to Hart's line, where mucosal epithelium gives way to skin on the outer surface of the labia minora. With more specific regard to the vagina, embodiments of the method comprise treating the lower portion of the vagina, a portion extending from the introitus to a location from about 2 cm to about 4 cm inward from the introitus, in other embodiments the location may extends inward as far as about 6 cm. With regard to the circumference of the inner wall of the vagina, a clock-position reference scheme is helpful. The urethra lies next to the anterior wall of the vagina, the location of the vaginal wall nearest the urethra and urethral opening may be considered 12 o'clock. With this reference point, the target tissue of embodiments of the invention include the approximately 300 degree arc between 1 o'clock and 11 o'clock. Embodiments of the invention do not include treating the approximately 60 degree arc between 11 o'clock and 1 o'clock because the practice of this invention is not directed toward tissue in the vicinity of the urethra.

Embodiments of the method include heating the target zone with radiant energy, typically radiofrequency (RF) energy, but other embodiments may use microwave or ultrasound energy. The method includes contacting the mucosal epithelium with a treatment tip that has an energy delivering element and a cooling mechanism. By delivering energy to the tissue while cooling the epithelial surface, a reverse thermal gradient is created. The RF energy penetrates through the cooled epithelium and into the underlying target tissue, and heats the tissue.

A zone of tissue that is heated within the target tissues to a threshold level, i.e., to a therapeutic temperature that causes remodeling is termed a therapeutic zone. Not all tissue within the target tissue necessarily reaches this threshold level of heat. In some cases, cooling from the treatment tip may penetrate into the target tissue, and in this situation, the presence of cooled tissue may have an effect on the therapeutic zone, by moving it deeper within the target tissue, for example, or by constraining its volume.

Energy delivered from the treatment tip may heat the target tissue to a temperature as high as about 80 degrees C. In some embodiments, therapeutic temperature may range between about 45 degrees C. and about 80 degrees C. In other embodiments, the therapeutic temperature may range between about 50 degrees C. and about 75 degrees C. In still other embodiments, the therapeutic temperature may range between about 55 degrees C. and about 70 degrees C. Heating is a process subject to feedback control during a treatment procedure, so as to keep the temperature within a predetermined temperature range. Feedback may be provided by one or more thermistors (thermal sensors) or impedance monitors. The treatment tip may cool the epithelium to a temperature between about 0 degrees C. and about 10 degrees C. A reverse thermal gradient, accordingly may be represented a low temperature of between about 0 degrees C. and about 10 degrees C. at the mucosal epithelium, and a high temperature of between 45 degrees C. and about 80 degrees C. in the target tissue. During a typical procedure, according to embodiments of the invention, any period of heating is accompanied by cooling; however cooling may also precede heating, and follow heating.

Methods of treatment comprise contacting the treatment tip to a contact site on the mucosal epithelium. The contact site conforms to the dimensions of the treating surface of the treatment tip. During the course of a single treatment, as for example would occur to a visit to a medical office, typically a plurality of contact sites are treated. During a procedure, a single contact site may be contacted multiple times. The summed total of mucosal contact sites comprises a treatment area. Such an area, comprising multiple contact sites may be recorded on a grid. The method may be applied on more than one occasion; a patient may return to her physician at a later date when the effects of a previous treatment may be evaluated and a treatment repeated. The treatment areas of the separate procedures may be the same, be different, or overlap.

Remodeling genital tissue, per embodiments of the invention may include heat-denaturing collagen within collagen-rich areas in the target tissues. Inasmuch as the overlaying mucosal epithelium is cooled by the method, it does not get heated, and is substantially unaffected by the method. Remodeling of target tissue within the therapeutic zone may occur substantially during the time when the tissue is being heated. Remodeling may also occur substantially after the heating has occurred, for example days or weeks later. Such remodeling comprises biological healing responses to the stress of heating, and such responses may include the deposition of new collagen. Whether by denaturation of existing collagen, or by later deposition of new collagen, the effect of remodeling on the tissue is generally one of tissue contraction or tightening. Thus, embodiments of invention comprise tightening the vagina and the introitus. The effect of vaginal childbirth on the vagina and introitus is a loosening of these tissues. Inasmuch as the method comprises tightening these tissues, the method has a rejuvenating effect in that it remodels the tissue toward the conformation it had prior to having experienced vaginal childbirth.

INCORPORATION BY REFERENCE

All publications and patent applications mentioned in this specification are herein incorporated by reference in their entirety to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 5A shows a single monopolar electrode, FIG. 5B shows a single bipolar of electrodes, and FIG. 5C shows multiple pairs of bipolar electrodes.

FIG. 6A shows an electrode with a flat surface, and FIG. 6B shows an electrode with a curved surface.

DETAILED DESCRIPTION OF THE INVENTION

Apparatus

Figure 1:
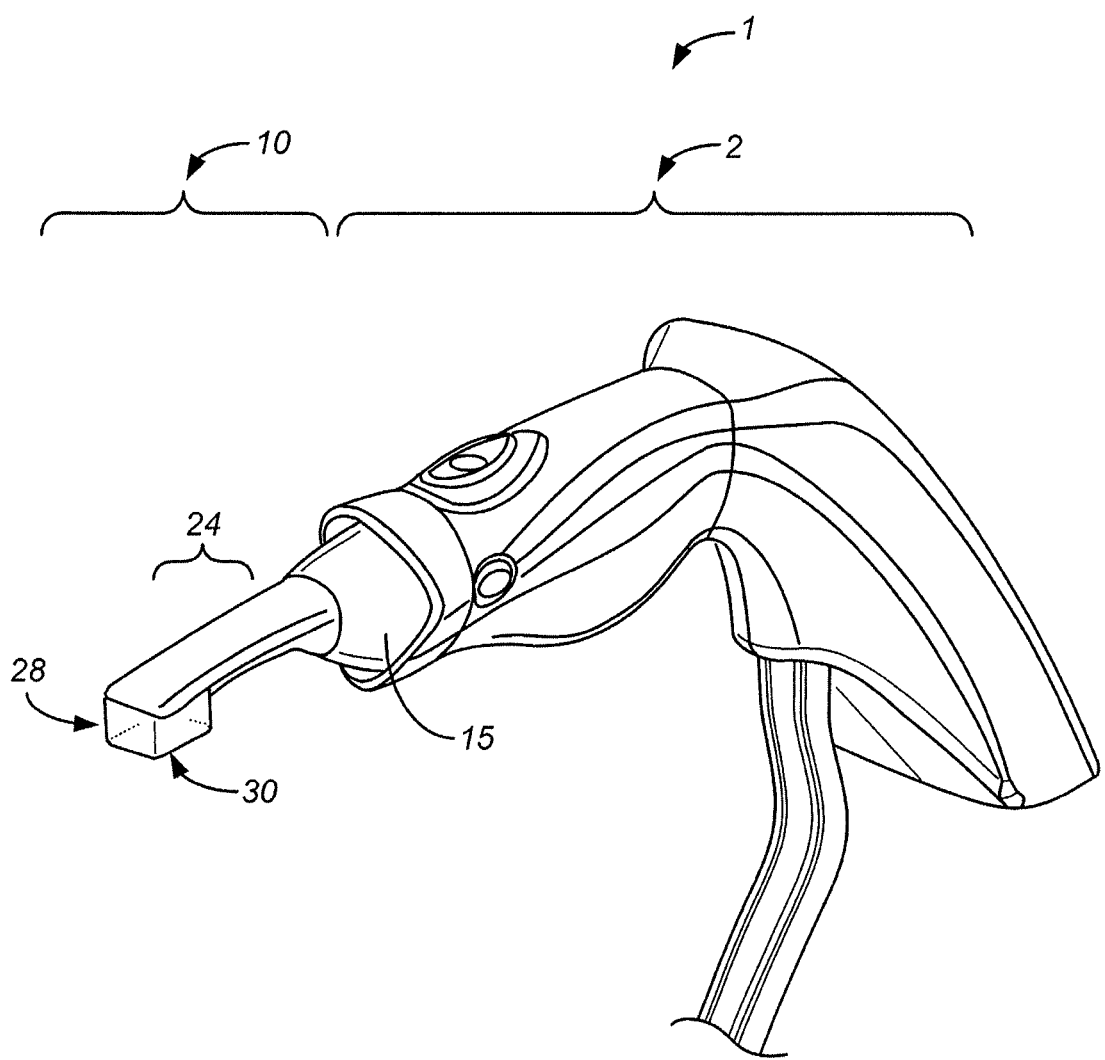
FIG. 1 is a perspective view of an apparatus for applying radiant energy to the target tissue while cooling the epithelium in order to remodel genital tissue, shown are a hand piece and a connected treatment tip.

Embodiments of the present invention include an apparatus and method for remodeling female genital tissue by applying heat to a target tissue underlying the surface mucosal epithelium, while cooling the surface epithelium itself. The apparatus and methods build on those of prior art such as those described by Knowlton, including US 2004/0000316, and others cited in the background, all incorporated by this reference, but include novel features in the apparatus and methods that are configured and adapted to particulars of the female genital treatment site, the mucosal epithelium contacted by the present apparatus, and the underlying target tissue that is remodeled according to aspects of the invention. FIG. 1 shows an apparatus 1, which comprises a hand piece 2 and a treatment tip 10. The hand piece 2 is adapted to be held by an operator, such as a physician, and may include connections to a larger supporting system (not shown), or, in some embodiments, it may be operable as self-sufficient independent device. FIG. 1 shows the connector portion 15 of the shaft of the treatment tip, the narrow midsection 24, and the distal portion 28, which includes the energy delivery element 30.

Figure 2:
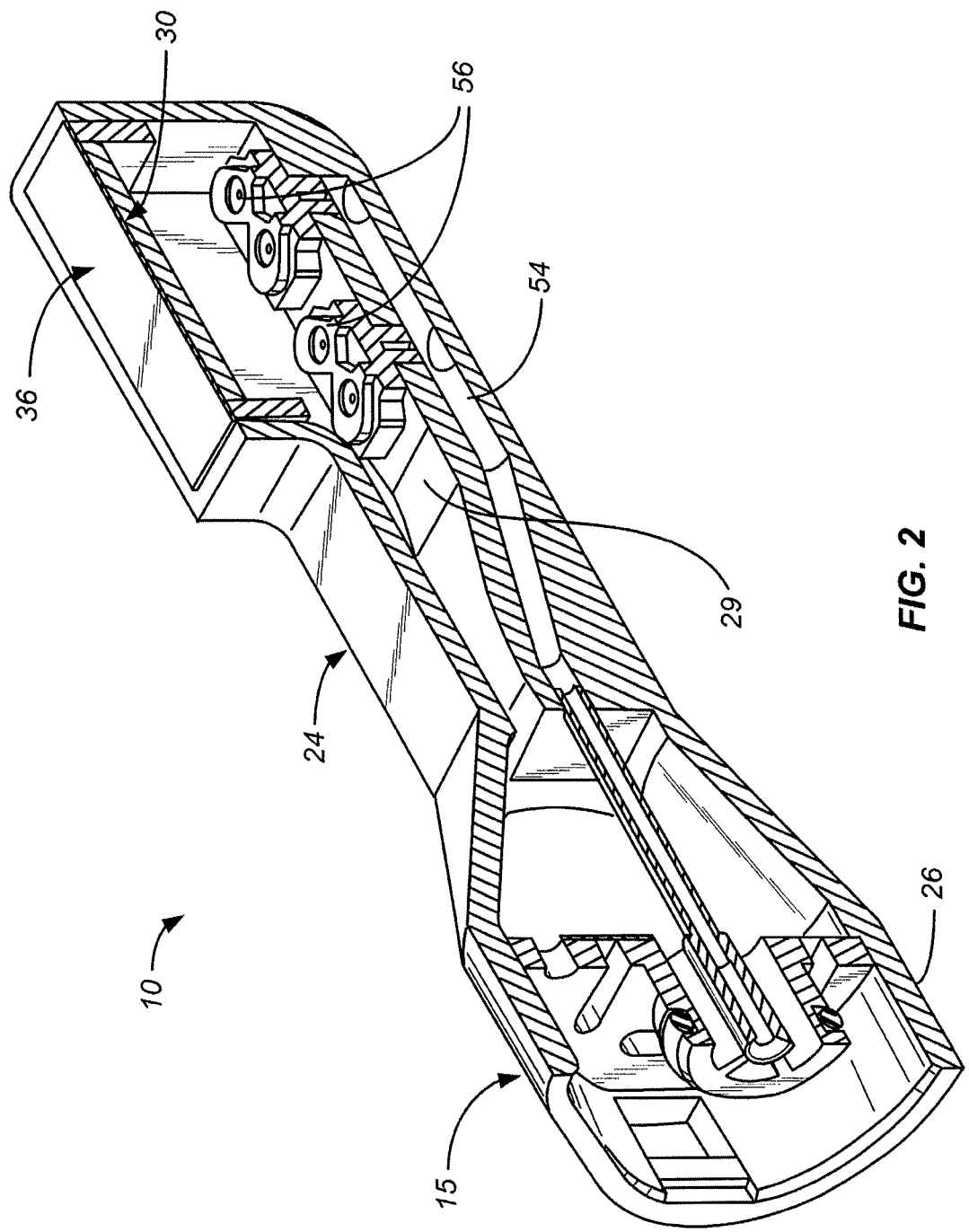
FIG. 2 is an exposed perspective view of a treatment tip embodiment.
Figure 3:
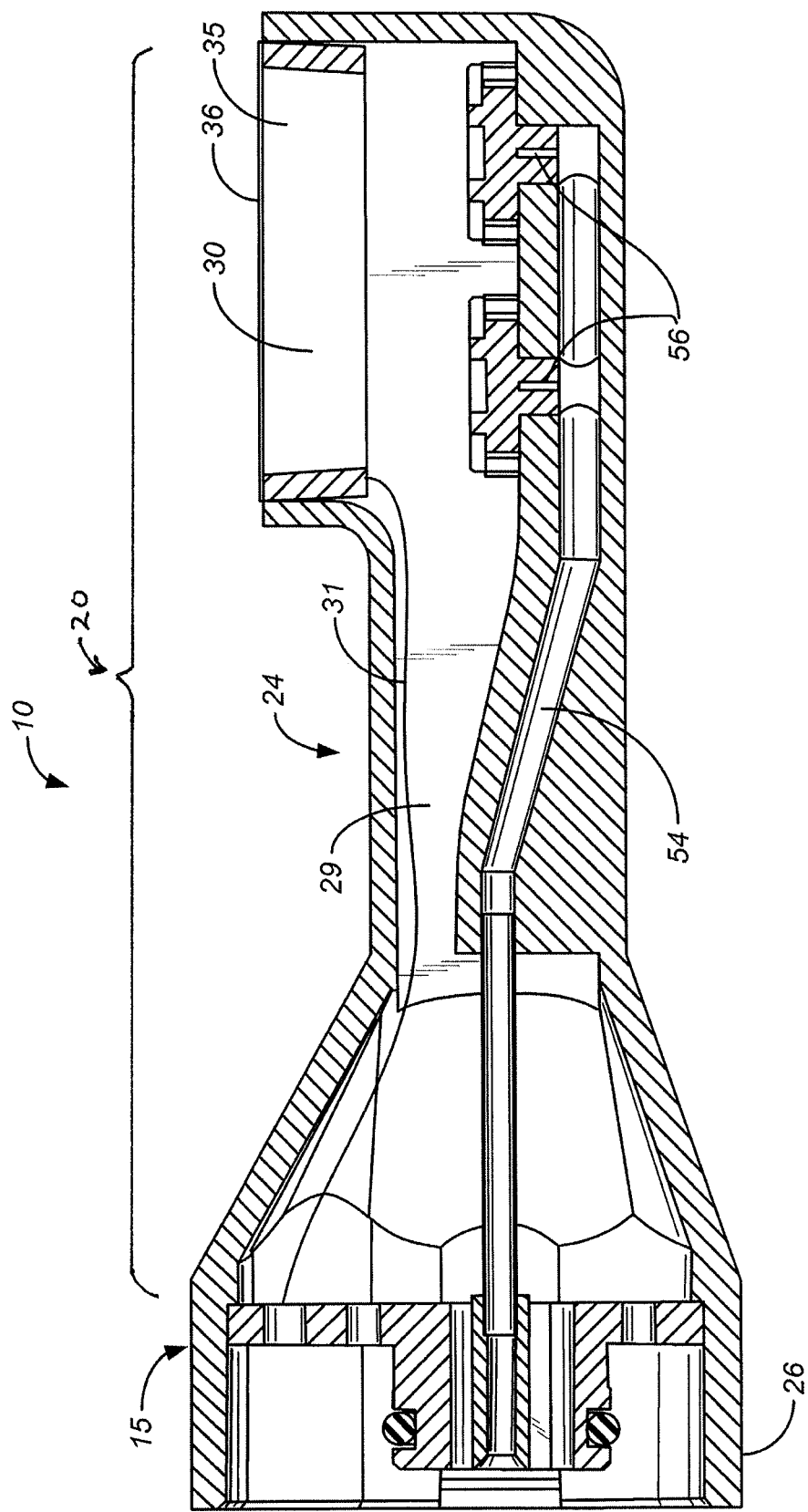
FIG. 3 is an exposed side view of a treatment tip embodiment.
Figure 4:
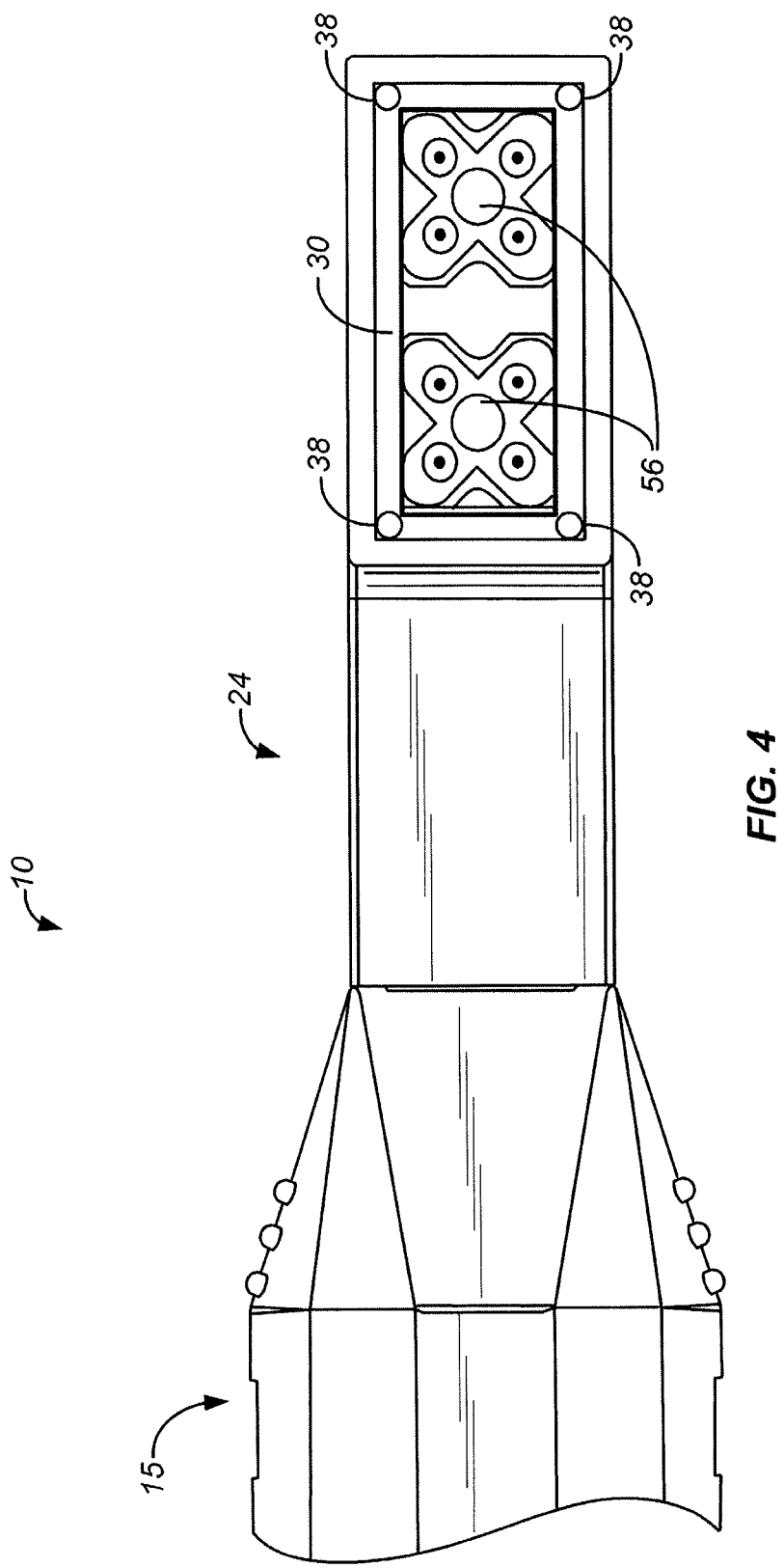
FIG. 4 is frontal cutaway view of the treatment tip, showing cooling nozzles that underlay the energy delivery element that contacts the epithelium
Figure 5A:
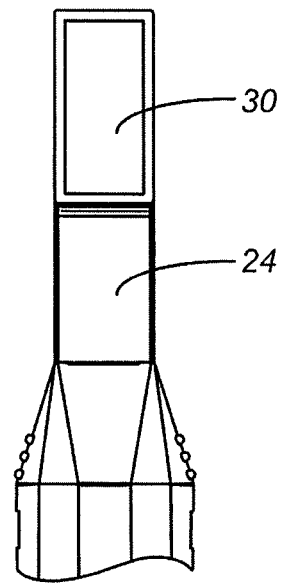
FIGS. 5A, 5B, and 5C show frontal views of the treatment tip embodiments.
Figure 5B:
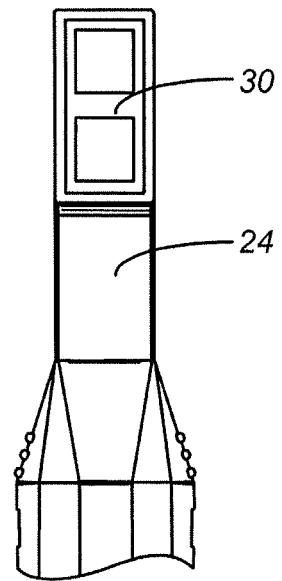
Figure 5C:
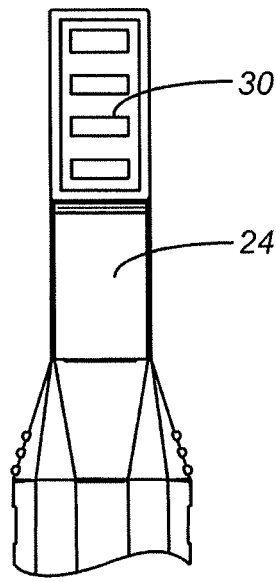

FIGS. 2-5C provide various views of the treatment tip. FIG. 2 provides an exposed view from a perspective proximal to the tip, FIG. 3 is an exposed view from a side perspective, and FIG. 4 is a frontal view directed toward the energy delivery element, exposed so as to reveal the nozzles directly below the energy delivery element. FIGS. 5A-5C show embodiments of the treatment tip that vary with respect to the type of energy delivery element (i.e., radiofrequency electrodes, variously monopolar, a bipolar pair, and multiple biopolar pairs). The treatment tip 10, depicted in greater detail in FIGS. 2-5C includes a housing 26, a connector portion 15, and an energy delivery element 30, which receives input through wire 31 (FIG. 3). The treatment tip as a whole is designed as a quick connect/disconnect unit with respect to its attachment to the base hand piece 2. The connection of the treatment tip 10 to the hand piece 2 is by way of the connector portion 15 of the treatment tip. The housing 26 defines an interior space 29 which extends forward from the connector portion 15 to the distal end 28 of the treatment tip. The energy delivery element 30 is side-mounted with respect to the linear axis of the tip, configured to face outward on a side on the distal portion 28 of the tip. By a side-mount, or by mounted so as to face a side of the treatment tip, it is meant that the energy delivery element 30 is configured to be approximately parallel to the linear axis of the shaft 20.

Between the connector portion 15 and the distal portion 28 of the tip is narrowed mid-section mid-portion 24, such narrowing or tapering on the same side as that which the energy delivery element 30 faces (narrowing may occur generally in the midsection 24, but embodiments typically include the narrowing at least on the same side as the energy delivery element). The side-mounted configuration of the energy delivery element 30 and the tapered section 24 of the tip both are adapted to optimize the contact of the energy delivery element to the epithelial surfaces of the female genitalia, in particular to those of the vagina. Details of the female genitalia are described further below. For the purpose of describing the advantage of a side placement 22 and the tapered section 21 of the shaft, of the canal-like aspect of vagina and entry into it with an instrument that engages the side of the canal are considered. An elongate structure best suited for entry into the vagina, and to make a substantially flat or surface-to-surface parallel contact with the side of the vagina, a side mounted energy delivery unit is advantageous. An advantage conferred by parallel contact is that contact pressure is distributed equally across the contact area, with no pressure biased against any side of the contact site. With such a uniformly pressured contact occurring, so too is energy uniformly directed to underlying target tissue. The narrow mid-section 24 of the shaft further provides a functional advantage to the tip 10 in that it allows the energy delivery element 30 at the distal portion 28 of the tip to project forward from the body of the shaft, such projection allowing the physician operating the apparatus to make contact to epithelium with appropriate pressure, to make the contact more discrete, to make the contacting flat, and to better visualize the contact.

The overall length of the treatment tip 10, from the base of the connector portion 15 to the foremost point of the distal portion 28 is designed such that the side mounted energy delivery element 30 reaches the innermost region of the vagina that is treated by the tip. Accordingly, embodiments of the tip may have an overall length of between about 2.75 inches and 4.25 inches. Particular embodiments have an overall length of between about 3 inches and about 4 inches. Still more embodiments have an overall length of between about 3.25 inches and about 3.75 inches. This overall length is appropriate for providing the treatment tip access the lower portion of a gently unfolded vagina.

The energy delivery element 30 also has dimensions advantageously adapted to making appropriately flat contact with the vaginal wall. The width of the element, an RF electrode in typical embodiments, in some embodiments is between about 0.7 cm and about 1.3 cm. In other embodiments, the width is between about 0.8 cm and about 1.2 cm. In still other embodiments, the width is between about 0.9 cm and about 1.1 cm. In some embodiments, the length of the energy delivery element 30 is between about 2 and about 3 cm. In other embodiments, the length is between about 2.25 cm and about 2.75 cm. The constraints on the length are related to the advantageous aspect of being able to make contact at particular sites on the mucosal epithelium, to avoid contact with other sites, deeper in the vagina, where it is not desired to make contact, and generally to make contact discretely and efficiently at the desired treatment area. The method of treatment typically comprises treating the vagina at a point no deeper than about 3.5 cm in from the introitus. The constraints on the width of the energy delivery element related, as described above, to the desirability of being able to make a substantially flat contact with the inner aspect of a curved surface. By constraining the width of the contact site, an increased pressure or closeness of contact that could occur along lengthwise edges is minimized.

Figure 6A:
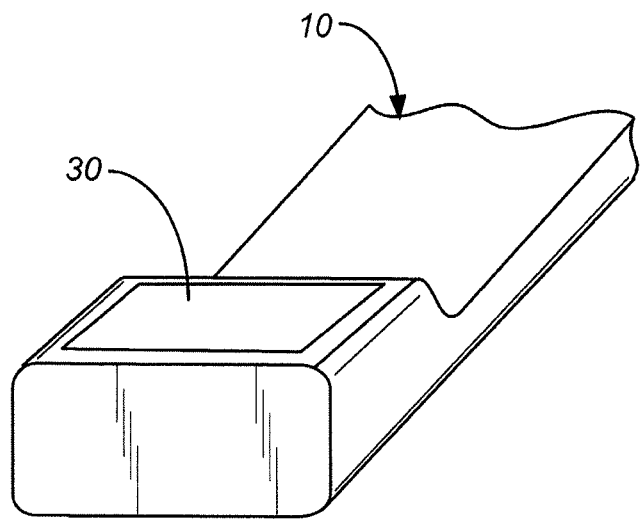
FIGS. 6A and 6B show front perspective views of two embodiments of a treatment tip, treatment side facing up, where
Figure 6B:
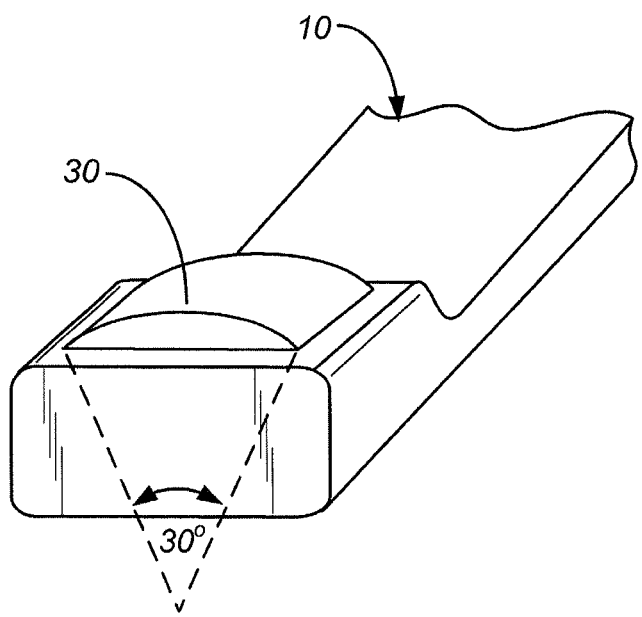

In embodiments depicted to this point, the energy delivery element has had a flat configuration. FIGS. 6A and 6B show another embodiment of the treatment tip 10, where the energy delivery element 30 takes a curvilinear form. In other embodiments the energy delivery element comprises a curved surface such it includes a curvature radially with respect to the linear axis while remaining parallel to the linear axis, the form representing an arc of a cylinder. FIG. 6A shows a treatment tip embodiment where the energy delivery element is flat, while the embodiment in FIG. 6B has a curved surface, the curve being radial with respect to the linear axis of the tip. The arc of the curvature may be as large as approximately 30 degrees. Some embodiments may include a curvature of about 30 degrees. This 30 degrees of curvature is adapted to fit the curvature of the vaginal wall.

Accordingly, various configurational and dimensional aspects of the treatment tip 10 and the energy delivery element 30 are advantageous for the method of remodeling genital tissue. These features are particularly suited for treating the vaginal wall, but also are appropriate for treating mucosal epithelial surfaces of female genitalia outside the vagina. As described above, these features include (1) the side-facing orientation of the energy delivery element with respect to the linear axis of the treatment tip and its shaft, (2) the overall length of the treatment tip from its proximal end to the distal end, (3) the narrow portion 24 of the tip which allows the energy delivery element to project forward from a background structure, rather than being in contiguous plane with surrounding structure, (4) the surface dimensions of the energy delivery element, particularly the width, which allow for substantially flat contact with the vaginal wall in the case of a flat energy delivery element 30, and (5) in the case of embodiment with a curved energy delivery element, a particularly close fit between the energy delivery element and the vaginal wall is achievable. All such enumerated features contribute to a uniformly-distributed contact between the energy delivery surface and the mucosal epithelium, such uniform fit diminishes the likelihood of edge-biased contact that could harm the epithelium, and affirmatively promotes uniform distribution of energy across the area of site where the energy delivery element contacts the epithelium and through which energy radiates into the underlying target tissue. Uniformity in flux across a surface area promotes an advantageous uniformity, consistency, and predictability in the remodeling response. Further, and equally important, small variation in flux also minimizes occurrence of damage, either to the epithelium or the target tissue, that can occur when large excursions in energy flux include, as they inevitably do, areas which receive high rates of energy flux.

As seen in FIGS. 2 and 3, the interior space 29 of the tip accommodates a cooling system to cool the energy delivery element, which comprises a cooling lumen 54 for conveying cooling fluid 52 to nozzles 56. The cooling fluid typically comprises a refrigerant, as exemplified by 1,1,1,2-tetrafluoroethane (R 134A), which is stored in a reservoir (not shown) under pressure, and conveyed through a lumen 54 to nozzles 56. The nozzles are configured within the interior space 29 in the distal portion 28 or the tip 10 under the inner surface of the energy delivery element 30. On release of the refrigerant from the nozzles, it sprays onto the interior surface and cools the element as the refrigerant undergoes a liquid to gas transition. The exterior surface of the energy delivery element, when in contact with an epithelial mucosal surface as during the practice of method embodiments of the invention, cools the epithelial surface upon such contact. This surface cooling prevents the build up of heat on the mucosal surface, the energy being delivered by the delivery element passes through the mucosal surface and into the underlying tissue targeted by the invention, which is then heated.

The energy delivery element 30 may be any of an RF electrode, a microwave emitter, or an ultrasound emitter. Embodiments that include an RF electrode will be described in some detail. The RF electrode, in some embodiments, is a capacitive electrode, which capacitively couples to the mucosal epithelium. The RF electrode, without limiting the scope of the invention, may have a thickness in the range of about 0.01 to about 1.0 mm.

The RF electrode 30 has a conductive portion 35 facing the interior space 29 within the treatment tip, and a dielectric portion 36 facing the exterior of the tip. Conductive portion 35 comprises a metal, exemplary metals including copper, gold, silver, and aluminum. Dielectric portion 36 may comprise a variety of different materials including, by way of example, polyimide, Teflon™ and the like, silicon nitride, polysilanes, polysilazanes, polyimides, Kapton and other polymers, antenna dielectrics and other dielectric materials well known in the art. Other exemplary dielectric materials include polymers such as polyester, silicon, sapphire, diamond, zirconium-toughened alumina (ZTA), alumina and the like. Dielectric portion 36 covers the conductive portion 35, and is disposed between conductive portion 35 and the patient's tissue during treatment. In another embodiment, RF electrode 30 is made of a composite material, including but not limited to gold-plated copper, copper-polyimide, silicon/silicon-nitride and the like. In one embodiment, conductive portion 35 adheres to dielectric portion 36 which can be a substrate with a thickness, by way of example and without limitation, of about 0.001". This embodiment is similar to a standard flex circuit board material commercially available in the electronics industry. In this embodiment, dielectric portion 36 is in contact with the mucosal epithelium, and the conductive portion 35 is separated from the mucosal epithelium.

Generally, RF electrodes 30 can be either monopolar or bipolar. In the monopolar mode, RF current flows through body tissue from a return electrode which can be in a form of a conductive pad applied to another portion of the patient's body. FIGS. 5A-5C show various embodiments of electrodes from a facing perspective, for example FIG. 5A shows a tip with a monopolar pair of electrodes, FIG. 5B shows a bipolar pair, and FIG. 5C shows a tip with multiple bipolar pairs. Additionally, the electrode may be equipped with an integrated EEROM (Electrically Erasable Read Only Memory, also known as EEPROM) programmable memory chip at any suitable location within the treatment tip (not shown). Such a chip may provide identifying information or other information about the operational status or configuration parameters of the RF electrode to the system, such parameters may include, by way of example, the type and size of the electrode, the number of times the energy delivery element has been fired, and the like. Additionally, thermistors (thermal sensors) 38 (shown in FIG. 4) may be provided at each corner of an RF electrode, or otherwise in close proximity to the electrode, to provide feedback to the system on the temperature at their location.

In some embodiments, the treatment tip as a whole is designed as a single-use disposable component, while the hand piece 2 is typically a reusable instrument. The single-use and disposable aspects of treatment tip 10 are in accord with its designated use in a single procedure, in the context of a female patient having a procedure, per embodiments of the method further described below, in a medical setting. Accordingly, the entirety of construction and components of the treatment tip retain their integrity through sterilization procedures, and the tip is typically packaged singly in a container or a wrap that preserves the sterile integrity of the tip until such time when it is unwrapped and connected to the hand piece 2 in preparation for a treatment procedure. Embodiments of the treatment tip 10 are modular in that they have a common connector portion 12 but may have variations in the shaft portion 20 and energy delivery elements 30 and cooling mechanism components, such as the fluid 52 or nozzles 56.

Electronic Support System for the Apparatus

The apparatus 1 is included in a larger electronic system (not shown) with features well known in the art. Embodiments comprise a power source, an RF power source in typical embodiments; it feeds energy to an RF power generator and power flows therefrom to RF electrodes 30. A multiplexer measures current, voltage and temperature, at the thermal sensors 38 associated with to each RF electrode 30. The multiplexer is driven by a controller, which can be a digital or analog controller, or a computer with software. When controller is a computer it can include a CPU coupled through a system bus. On the system there may also be a keyboard, disk drive, or other non volatile memory systems, a display, and other peripherals, as are well known in the art. Also coupled to the bus may be a program memory and a data memory.

An operator interface includes operator controls and a display. The controller can be coupled to different types of imaging systems including ultrasonic, thermal sensors 38, and impedance monitors 39. Current and voltage are used to calculate impedance. A diagnostic phase can be initially run to determine the level of treatment activity. This can be done through ultrasound as well as other means. Diagnostics can be performed both before and after treatment.

Thermal sensors 38 measure voltage and current as delivered to the desired treatment site; the output for these sensors is used by a controller to control the delivery of RF power, which can also control temperature and power. An operator set level of power and/or temperature may be determined to provide operating limits that will not be exceeded. The controller maintains the set level under changing conditions. The amount of RF energy delivered controls the amount of power. A profile of power delivered can be incorporated in the controller, as well as a preset amount of energy to be delivered. Feedback control can be based on monitoring of impedance, temperature, or other indicators, and occurs either at the controller or at RF generator, if it incorporates a controller. For impedance measurement, this can be achieved by supplying a small amount of non therapeutic RF energy. Voltage and current are then measured to confirm electrical contact.

Circuitry, software and feedback to controller result in full process control and are used to change power, the duty cycle, monopolar or bipolar energy delivery, flow rate and pressure, and can also determine when the process is completed through time, temperature and/or impedance. These process variables can be controlled and varied in accordance with tissue temperature, as monitored at multiple sites on contacting exterior surface 34, as well as by monitoring impedance to current flow at each RF electrode 30, indicating changes in current carrying capability of the tissue during the process. Further, a controller can provide multiplexing, monitor circuit continuity, and determine which RF electrode 30 is activated.

Thermal sensors 38 can be thermistors, which have a resistance that varies with temperature. An analog amplifier can be a conventional differential amplifier circuit for use with thermistors and transducers. The output of the analog amplifier is sequentially connected by an analog multiplexer to the input of an analog digital converter. The output of the amplifier is a voltage, which represents the respective sensed temperatures. The digitized amplifier output voltages are supplied by analog to digital converter to a microprocessor, which calculates the temperature or impedance of the tissue. In some embodiments, the microprocessor can be a type 6800, however, any suitable microprocessor or general purpose digital or analog computer can be used to calculate impedance or temperature. The microprocessor sequentially receives and stores digital representations of impedance and temperature. Each digital value received by the microprocessor corresponds to different temperatures and impedances.

Calculated temperature and impedance values can be indicated on a display. Alternatively, or in addition to the numerical indication of temperature or impedance, calculated impedance or temperature values can be compared by the microprocessor with temperature and impedance limits. When the values exceed predetermined temperature or impedance values a warning can be given on the display and additionally, the delivery of RF energy to its respective electrode can be decreased or multiplexed to another electrode. A control signal from the microprocessor can reduce the power level by the RF generator, or de-energize the power delivered to any particular electrode. The controller 68 receives and stores the digital values that represent temperatures and impedances sent. Calculated surface temperatures and impedances can be forwarded by the controller to the display. If desired, the calculated surface temperature of the vaginal mucosal tissue layer is compared with a temperature limit and a warning signal can be sent to the display. Similarly, a control signal can be sent to the RF power source when temperature or impedance values exceed a predetermined level.

Methods

Embodiments of the invention provide a non-surgical method and apparatus for remodeling the tissues of the female genitalia by applying heat to a target tissue underlying the surface mucosal epithelium, while cooling the surface epithelium itself. Typically, the tissues are those of women who have had one or more vaginal births, and whose tissues have been stretched by giving birth. In particular, the target tissues (FIG. 8) are the connective tissue layers such as the lamina propria or submocosa 102 and the muscularis 104 underlying the mucosal epithelium 100 of genital tissues. Particular features or areas of genital tissue (FIG. 7) having an epithelial surface include the vulva and the vagina 112, and the introitus 114, the entrance to the vagina and a demarcation between the internal and external genitalia.

The heating of target tissue, per embodiments of this invention includes raising the temperature of the target tissue to as high as 80 degree C. Temperature is raised to a level that is therapeutic, i.e., to a temperature that causes remodeling, as described herein. That portion of the target tissue which attains the therapeutic temperature, for a sufficient time, is termed the therapeutic zone within the target tissue. The therapeutic temperature, in some cases may be only as high as 45 degrees C., or as high as 80 degrees C. The inventive method, therefore includes heating target tissue to as high as 80 degrees C. Per embodiments of the invention, target tissue may be heated to a temperature between about 45 degrees C. and about 80 degrees C. In other embodiments, the target tissue temperature may be heated to a temperature between about 50 degrees C. and about 75 degrees C. In still other embodiments, the target tissue may be heated to a temperature between about 55 degrees C. and about 70 degrees.

The vagina is a fibromuscular tube, lined with stratified squamous epithelium, that connects the external and internal organs of the female reproductive system. The vagina runs obliquely upwards and backwards at an angle of about 45 degrees between the bladder in front and the rectum and anus behind. In an adult female the anterior wall is about 7.5 cm long and the posterior wall is about 9 cm long. The difference in length is due to the angle of insertion of the cervix through the anterior wall. More particularly with regard to the vagina, embodiments of the invention comprise remodeling the lower portion of the vagina, the lower portion representing, the lower being that portion immediately inward from the introitus. Thus, according to embodiments of the invention, the portion of the vagina to be treated is a region between the introitus and a position located no further than about 3 to about 4 cm inward from the introitus. With regard to the circumferential aspects of the vagina, locations along the circumference of the vaginal wall may be assigned a clock position (see reference clock dial 136, in FIG. 7) such that the circumferential point closest to the urethra is at 12 o'clock. Using this orientation, embodiments of the invention comprise treating and remodeling the vagina over the 300 degree circumferential arc from about 1 o'clock to about 11 o'clock.

Figure 7:
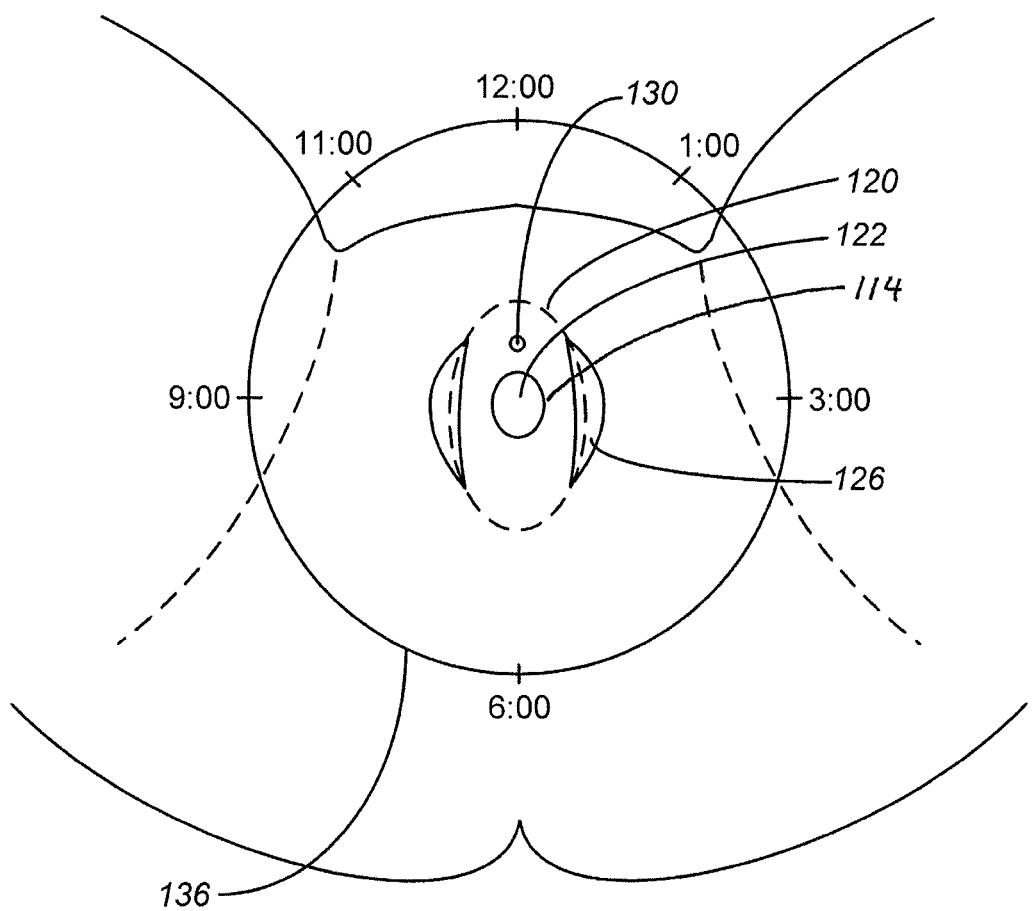
FIG. 7 is a schematic view of female genitalia depicting the mucosal epithelial surfaces that overlay the target tissue, as well as an orienting clock to provide a circumferential reference scheme for the vagina wall.

The mucosal epithelium of vulvar tissue outside the vagina and the introitus includes the labia minora, or that portion of the vulva extending outward from the introitus to Hart's line, the boundary where mucosal epithelium and labial skin meet (FIG. 7). The mucosal epithelium and the skin, while contiguous, are embryologically and histologically distinct. The portion of the female genitalia that are covered by epithelium is also substantially defined by the bounds of the vestibule, which extends outward or down from the hymenal ring at the top of the vagina, radially beyond the introitus, including the portion of labia minora located within Hart's line 120. The target tissue of embodiments of this invention include the connective tissue underlying these mucosal epithelial surfaces of the genitalia which, progressing down from the epithelial surface, are known as the lamina propria 102 and the muscularis 104 (FIG. 8), respectively (see, for example, Netter, Atlas of Human Anatomy, 4th edition, Saunders, 2006). The lamina propria includes a mixture of cells types that populate connective tissue, such as fibroblasts, and the muscularis is a layer of smooth muscle. Collagen is secreted or deposited into the extracellular space in these tissues by cells such as fibroblasts. These described target tissue layers below the epithelium overlay deeper tissues, including endopelvic fascia, which are not a target tissue for embodiments of the present invention.

The remodeling of the connective tissue underlying the mucosal epithelial surfaces does not substantially affect the epithelium itself. The method and apparatus, as provided by embodiments of the invention are non-invasive and substantially non ablative of genital issue. The nature of the engagement between the apparatus and genital tissue is that of contacting a treatment tip to an epithelial surface of the genital tissue. Through such contact, the apparatus delivers heat to underlying tissue, while preventing the heating of the surface epithelium by cooling it.

In a particular embodiment, the invention provides a method and apparatus for remodeling vulvar and vaginal target tissue through the use of a radiofrequency (RF) energy source 30 (see the energy delivery element of FIGS. 1-5C) through the vaginal or vulvar mucosal epithelial tissue and to the respective underlying layers that are the target tissue of embodiments of the invention. Other embodiments may make use of other forms of energy, such as microwave or ultrasound. Impedance through mucosal epithelium is lower than that of skin, thus less energy is required to cause heating than would be required were skin being treated rather than mucosal epithelium.

The application of energy to the underlying connective tissue creates heat in the targeted tissue, and the heat is understood to have an immediate or nearly immediate effect of denaturing or partially-denaturing collagen in the tissue, this denaturation of collagen being a factor in the tissue remodeling. In other embodiments of the invention, the application of heat to the connective tissue during a treatment procedure is understood to result in a subsequent depositing of new or nascent collagen by cells of the connective tissue, as part of a biological process that may take place over the course of weeks or months following the procedure.

As provided by embodiments of the invention, remodeling of genital tissue, whether by denaturation of collagen in the tissue, or by subsequent deposition of new collagen in the tissue, results in a tightening of genital tissue, particularly that of the vagina and the introitus. A consequence of the heating of the target tissue may include a melting or denaturing of preexisting collagen in the tissue, which may reduce or compact the volume occupied by the collagen, the effect of which is to tighten surrounding tissue A longer term biological consequence of the heating may include a healing process in which there is an increase in the rate of cellular production and deposition into the extracellular space. Both types of responses, the near-immediate response of preexisting collagen, and the longer term increased amount of collagen are understood to contribute to an overall tightening of the target tissue.

The tightening of tissue is such that the remodeled genitalia assumes a rejuvenated form, a conformation of the genitalia as they were before having being stretched by vaginal birth. Remodeling of genital tissue, as practiced by embodiments of this invention, may be understood variously as contracting or tightening of tissue, this may apply to the vulva, the vagina, and the introitus. Genitalia rejuvenated by practice of embodiments of the invention, by virtue of the greater tightness of the remodeled vagina and introitus, for example, provide for increased pressure and friction during sexual intercourse, and accordingly may provide greater sexual satisfaction for a woman with such remodeled genitalia and for her sexual partner.

Embodiments of the invention provide a method and apparatus for creating a reverse thermal gradient that utilizes one or more RF electrodes 30, to convey energy that manifests as heat in the target tissue, and a mechanism to cool the epithelial surface above the targeted underlying layers. A purpose of cooling the epithelial surface is to protect it from potentially damaging effects of excess heat that would accumulate in the absence of cooling. The epithelial surface is thus a conduit for energy passing through to underlying layers, but the energy does not manifest in the form of increased temperature at the epithelial surface. As such, the epithelium itself is not damaged or substantially modified by the method. Such protection from heating may derive both from the heat-sink aspect of a cooled body, as well as an increase in tissue impedance that is associated with cooled tissue.

In some embodiments, the cooling mechanism of the apparatus includes a lumen 54 adapted to accommodate a cooling fluid conveyed to nozzles 56, which cool the energy delivery element 30 of treatment tip 10 of the apparatus. Embodiments of the method thus provide for contacting a contact site on a genital epithelial surface, the tip having the capability both to cool the surface epithelium and to heat the underlying tissue. The cooling fluid cools the treatment tip of the apparatus, as provided by embodiments of the invention; in turn, the surface of the cooled treatment tip cools the surface of the mucosal epithelium that the treatment tip contacts. As provided by embodiments of the invention, the epithelial surface may be cooled to a temperature range of about 0 degrees C. to about 10 degrees C. As energy from the tip passes through the mucosal epithelial surface, the underlying soft tissue may be heated to a temperature range of about 45 degrees C. to about 80 degrees C. Thus, a reverse thermal gradient is created, with a lower temperature at the mucosal epithelium, and a higher temperature in the underlying tissue.

In some embodiments the method includes feedback control mechanisms to control the heating such that temperature does not exceed a predetermined level. As provided by embodiments of the apparatus, the feedback is provided to RF delivery by thermal or impedance sensors. In other embodiments, the method may be controlled by delivering a predetermined total of amount of energy. In some embodiments the method may be controlled by delivering an amount of energy within a predetermined amount of time.

More specifically within the target tissue of the invention, a treatment zone may be defined, where the heat is particularly focused, or where the heat reaches a threshold temperature sufficient to cause remodeling. Such a treatment zone may be centered at a particular depth below the epithelium, and the treatment zone may have a particular range of depth, it may, for example be broadly distributed across the full range of the lamina propria and muscularis, or it may occupy a relatively flat zone. In some embodiments of the invention, cooling is allowed to proceed into the target tissue itself, below the epithelial surface, to form a cold-protected tissue zone. The cooling of a portion of the target tissue may have an effect on the therapeutic zone, such that the depth and range of the therapeutic zone may be modulated or shifted with respect to where it would be absent such cooling of a portion of the target tissue. If cooling penetrates to a given level in the target tissue to create a cold-protected zone, for example, the therapeutic zone may be pushed deeper into the target tissue. Further, lower temperature in general tends to contain the dissemination of heat, thus focusing the therapeutic zone into a narrower range of depth.

In typical embodiments of the invention, the method provides for surface cooling coincident with the time that heat is being delivered to underlying tissue. In some embodiments, in addition to cooling the surface while heating the underlying tissue, the method includes a period of cooling before the application of heat. In other embodiments, the method includes a period of cooling after the application of heat. In still other embodiments, the method includes cooling both before and after the application of heat.

Figure 8:
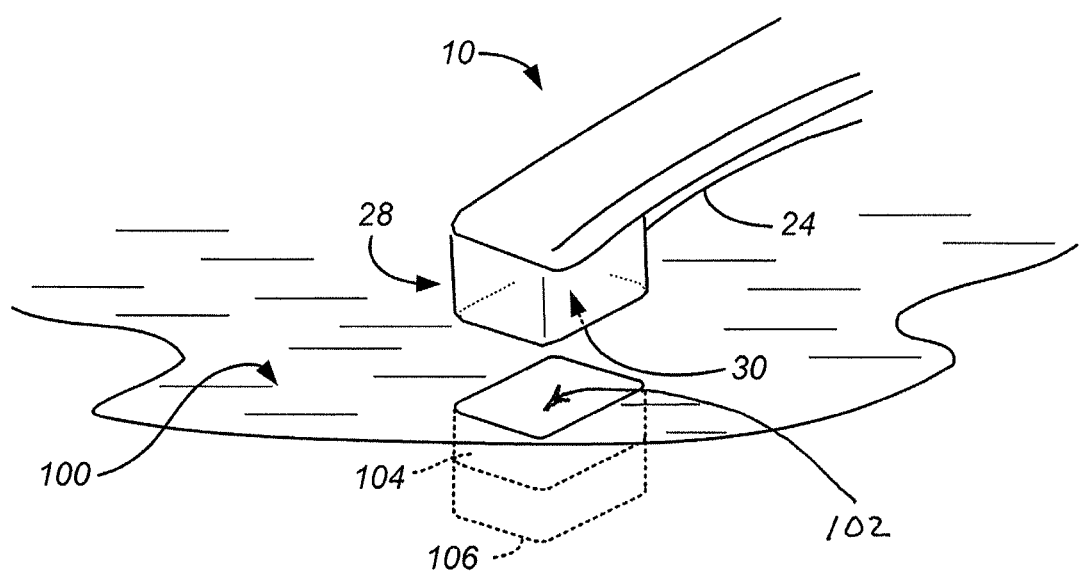
FIG. 8 shows a treatment tip contacting a genital epithelial mucosal surface and the underlying target tissue including the lamina propria and the muscularis.

As shown in FIG. 8, a treatment tip 10 of the apparatus contacts a contact site 102 on the genital epithelium 100, and such contact creating a site on the epithelium corresponding to the surface area within the outline of the profile of the treatment tip. FIG. 8 shows the distal end 28 of the tip, with the energy delivery element 30 (shown by dotted lines) facing toward the mucosal epithelium. Also shown below the contact site 102 (with dotted lines) are target tissue layers, the lamina propria 104 and the muscularis 106. In typical embodiments of the invention, the method includes making contact with the epithelium, delivering energy, and then moving the treatment tip to another contact site, and delivering energy there. A procedure, such as would take place in a visit to a medical office, would typically include a radial sequence of contacting the epithelium within the vagina and/or contacting other sites outside the vagina. During the same procedure, the treatment tip may be returned to the same contact point multiple times. The circumference of the lower portion of an unfolded vagina, gently stretched as it is during the practice of this method, is approximately 12 cm. Accordingly, with a treatment tip of about 1 cm in width, a series of about 10 contact sites allows completion of an 300 degree arc of the circumference, between the 1 o'clock and 11 o'clock positions. These dimensional considerations underlie the rationale for an embodiment of the treatment wherein the surface of the energy delivery element has a curvature of about 30 degrees, each contact site accounting for about 10% of the 300 degree arc.

Figure 9A:
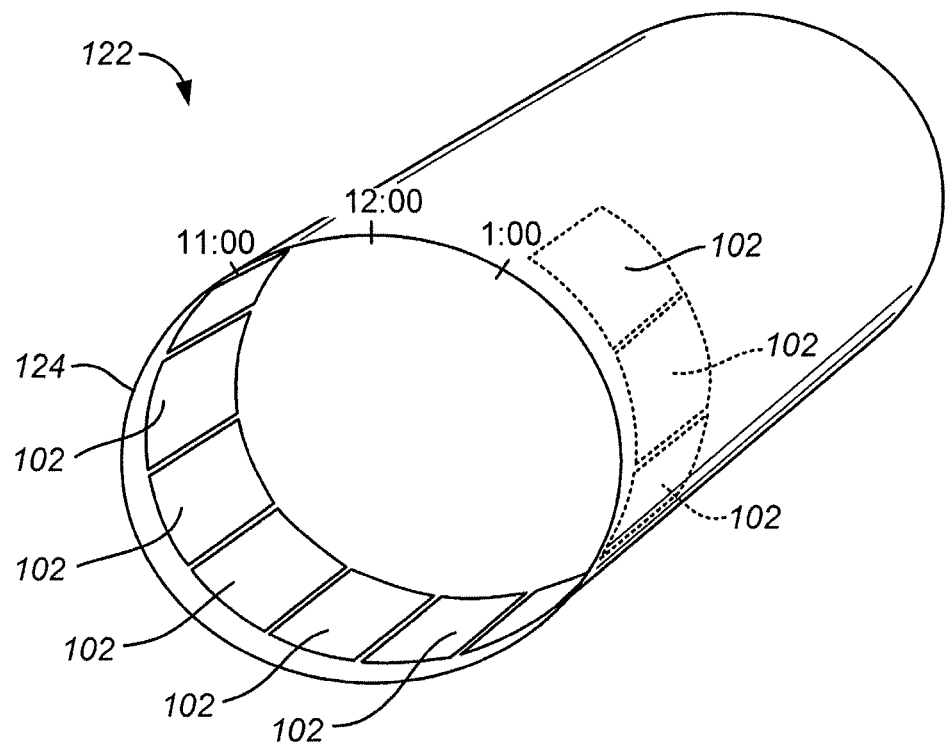
FIG. 9A depicts a treatment area of a mucosal epithelium comprising multiple contact sites.
Figure 9B:
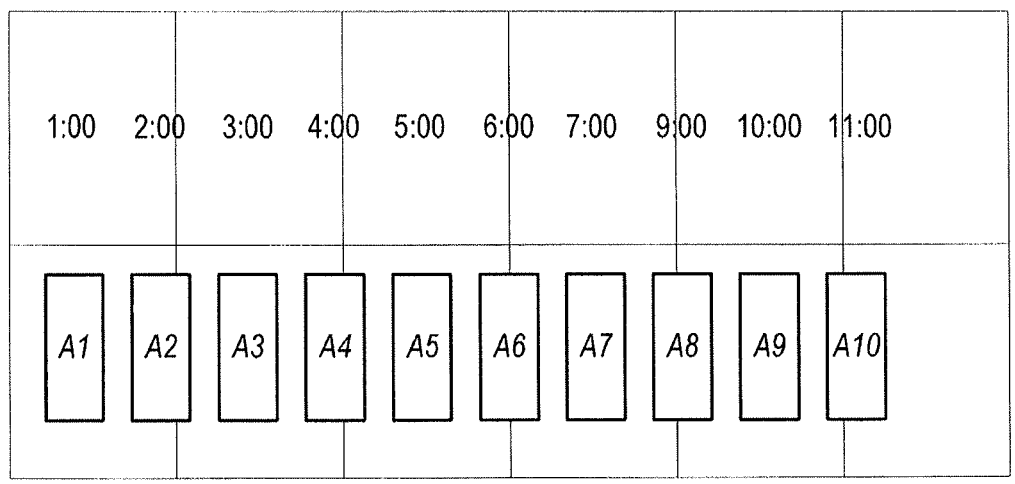
FIG. 9B depicts a representation of the treatment area as a mapping grid.

FIG. 9A is a schematic representation of a vagina 122, with the introitus 124 forming the entrance to the vagina. In a typical procedure, the treatment tip would contact various contact sites in the lower vagina, just inside the introitus. As shown in FIG. 9A, an accumulated set of contact sites 102 that have been treated by the treatment tip, and they collectively comprise a treatment area on the vaginal epithelium. In some embodiments of the method, a single radial row of sites is contacted, as shown in FIG. 9A. In other embodiments, one or more further rows could be included in a procedure, extending further into the vagina, so long as the treatment area remains in the lower portion of the vagina. Contact sites, per embodiments of the invention may include regions outside of the vagina, but within the bounds of Hart's line. Outside of the vagina, the treatment area will develop with a flatter aspect, in contrast to the inner radial configuration characteristic of the vaginal contact sites. As further provided by embodiments of the method and shown FIG. 9B, the contact sites may be recorded on a grid 115, the completed grid thus being a mapped representation of the treatment area, which can be referred to during evaluation of the remodeling at some time point following the treatment. As shown, the treatment grid may contain reference points with respect to the circumferential location on the vagina, as provided, for example, by the clock dial scheme.

As summarized above, a given treatment area will be treated during a single procedure during an office visit. The method further includes repetitions of such procedures, typically on another day, when the effects of the previous procedure may be evaluated. From such evaluation, judgment may be made with regard to re-treating a particular previously-treated area, or proceeding to treat other areas. Thus, as provided by embodiments of the method, one or more procedures during follow-up visits may variously include treating the same treatment area, treating an entirely different treatment area, or treating an overlapping treatment area, partially the same as previous area, and partially different.

Other variations of treatment tip design and associated methods can be employed to achieve the objectives of the invention without departing from the scope of the invention, as will be appreciated by those skilled in the art. The shape and dimensions of the tip can also be adjusted, as desired, to enhance the effectiveness of the treatment taking into consideration physiological and anatomical information. While various embodiments of the present invention have been shown and described herein, it will be obvious to those skilled in the art that such embodiments are provided by way of example only. Although the description has offered the theory that collagen denaturation underlies the remodeling of tissue brought about by practicing the invention, and theory has also been offered that tissue remodeling may occur as a result of the deposition of collagen by connective tissue at a time after the inventive procedure has been performed. Some theory has also been offered to explain the nature of the protection afforded to the mucosal epithelium by cooling it. Such theories has been offered to simply as possible theories of how the invention works and as an aid in describing the invention, however, it should be understood that such theories and interpretation do not bind or limit the claims with regard to tissue remodeling brought about by the practice of the invention. Numerous variations, changes, and substitutions will now occur to those skilled in the art without departing from the invention. It should be understood that various alternatives to the embodiments of the invention described herein may be employed in practicing the invention. It is intended that the scope of the invention, methods and structures within the scope of the invention includes equivalents.

What is claimed is:

1. An apparatus for remodeling a therapeutic zone within a target tissue, the target tissue comprising tissue underlying a mucosal epithelium of female genital tissue, the apparatus comprising:
   a treatment tip configured to releasably couple and decouple to a hand piece, the treatment tip comprising:
   an elongate shaft comprising a longitudinal axis, a proximal end, a distal end having a distal portion, and a narrow portion extending between the proximal end and the distal end, wherein the narrow portion narrows inwardly toward the longitudinal axis of the elongate shaft on a side of the elongate shaft, and
   a non-expandable side-facing energy delivery element comprising a metal RF electrode on the elongate shaft and proximal to the distal end of the elongate shaft, the side-facing energy delivery element being disposed only along the same side of the elongate shaft as the narrow portion, wherein the metal RF electrode is curvilinear such that it curves radially with respect to the longitudinal axis while extending in parallel with the longitudinal axis, wherein the energy delivery element is adapted to contact the epithelium,
   wherein the energy delivery element projects forward from the narrow portion on only a single side of the elongate shaft, and
   wherein the distal portion has a first surface and the narrow portion has a second surface, wherein the energy delivery element is only disposed on the first surface, wherein the first surface is substantially parallel to the second surface, and wherein the first surface is in a different plane than the second surface, allowing for the energy delivery element to contact the epithelium.

2. The apparatus of claim 1, wherein the metal RF electrode is configured to be substantially parallel to the longitudinal axis of the elongate shaft and has a length of between about 1 to 4 cm.

3. The apparatus of claim 1, wherein the metal RF electrode is configured to have a width of about 0.75 cm to about 1.25 cm.

4. The apparatus of claim 1, wherein the metal RF electrode is configured to have a length of about 1 cm to about 3 cm.

5. The apparatus of claim 1, wherein the metal RF electrode is configured to have a radial curvature with respect to the longitudinal axis of the elongate shaft of up to 30 degrees.

6. The apparatus of claim 1, wherein the metal RF electrode curves radially with respect to the longitudinal axis at an arc of about 30 degrees.

7. The apparatus of claim 1, wherein the narrow portion is proximal to the energy delivery element.

8. The apparatus of claim 1, further comprising a cooling system within the elongate shaft configured to cool the energy delivery element.

9. The apparatus of claim 8, wherein the cooling system comprises cooling fluid and at least one nozzle, the nozzle configured to spray the cooling fluid on the energy delivery element.

10. The apparatus of claim 1, wherein the RF electrode is a monopolar electrode.

11. The apparatus of claim 1, wherein the RF electrode is one electrode of a bipolar electrode pair of the energy delivery element.

12. The apparatus of claim 1, further comprising at least one thermister located in close proximity to the RF electrode.

13. The apparatus of claim 1, further comprising a programmable memory chip.

14. The apparatus of claim 1, further comprising the hand piece adapted to be held by an operator, wherein the treatment tip is connected to or configured to connect to a distal end of the hand piece and the hand piece.

15. The apparatus of claim 1, further comprising a connector portion at a proximal end of the treatment tip configured to removably connect the treatment tip to the hand piece.

16. The apparatus of claim 1, further comprising a dielectric on an exterior of the energy delivery element.

17. The apparatus of claim 1, wherein the metal RF electrode extends in an arc above the first surface of the distal portion.

18. The apparatus of claim 1, wherein the metal RF electrode has a width of between about 0.7 cm and 1.3 cm.

19. An apparatus for remodeling a therapeutic zone within a target tissue, the target tissue comprising tissue underlying a mucosal epithelium of female genital tissue, the apparatus comprising:
   a non-expandable treatment tip, the treatment tip comprising:
   an elongate shaft comprising a longitudinal axis, a proximal end, a distal end having a distal portion, and a narrow portion extending between the proximal end and the distal end, wherein the narrow portion narrows inwardly toward the longitudinal axis of the elongate shaft on a side of the elongate shaft,
   a connector portion at the proximal end of the elongate shaft, and
   a side-facing energy delivery element comprising a monopolar RF electrode on a distal end region of the elongate shaft and proximal to the distal end of the elongate shaft, the side-facing energy delivery element being disposed only along the same side of the elongate shaft as the narrow portion, wherein the RF electrode is curvilinear such that it curves radially with respect to the longitudinal axis while extending in parallel with the longitudinal axis, wherein the energy delivery element is adapted to contact the epithelium; and
   a hand piece adapted to be held by an operator and configured to releasably couple and decouple with the connector portion of the elongate shaft,
   wherein the energy delivery element projects forward from the narrow portion on only a single side of the elongate shaft, and
   wherein the distal portion has a first surface and the narrow portion has a second surface, wherein the energy delivery element is only disposed on the first surface, wherein the first surface is substantially parallel to the second surface, and wherein the first surface is in a different plane than the second surface, allowing for the energy delivery element to contact the epithelium.

20. The apparatus of claim 19, wherein the RF electrode is configured to have a width of about 0.75 cm to about 1.25 cm.

21. The apparatus of claim 19, wherein the RF electrode is configured to have a length of about 1 cm to about 3 cm.

22. The apparatus of claim 19, wherein the RF electrode is configured to have a radial curvature with respect to the longitudinal axis of the elongate shaft of up to 30 degrees.

23. The apparatus of claim 19, wherein the RF electrode curves radially with respect to the longitudinal axis at an arc of about 30 degrees.

24. The apparatus of claim 19, wherein the narrow portion is proximal to the energy delivery element.

25. The apparatus of claim 19, further comprising a cooling system within the elongate shaft configured to cool the energy delivery element.

26. The apparatus of claim 25, wherein the cooling system comprises cooling fluid and at least one nozzle, the nozzle configured to spray the cooling fluid on the energy delivery element.

27. The apparatus of claim 19, further comprising at least one thermister located in close proximity to the RF electrode.

28. The apparatus of claim 19, further comprising a programmable memory chip.

29. The apparatus of claim 19, further comprising a dielectric on an exterior of the energy delivery element.

30. The apparatus of claim 19, wherein the RF electrode has a length of between about 1 to 4 cm.

31. An apparatus for remodeling a therapeutic zone within a target tissue, the target tissue comprising tissue underlying a mucosal epithelium of female genital tissue, the apparatus comprising:
   a treatment tip, the treatment tip comprising:
   an elongate shaft comprising a longitudinal axis, a proximal end, a distal end having a distal portion, and a narrow portion extending between the proximal end and the distal end, wherein the narrow portion narrows inwardly toward the longitudinal axis of the elongate shaft on a side of the elongate shaft,
   a connector portion at the proximal end of the elongate shaft, and
   a side-facing energy delivery element comprising a monopolar RF electrode fixed on a distal end region of the elongate shaft and proximal to the distal end of the elongate shaft, the side-facing energy delivery element being disposed only along the same side of the elongate shaft as the narrow portion, wherein the RF electrode is curvilinear such that it curves radially with respect to the longitudinal axis while extending in parallel with the longitudinal axis, wherein the energy delivery element is adapted to contact the epithelium; and
   a hand piece adapted to be held by an operator and configured to releasably couple and decouple with the connector portion of the elongate shaft,
   wherein the energy delivery element projects forward from the narrow portion on only a single side of the elongate shaft, and
   wherein the distal portion has a first surface and the narrow portion has a second surface, wherein the energy delivery element is only disposed on the first surface, wherein the first surface is substantially parallel to the second surface, and wherein the first surface is in a different plane than the second surface, allowing for the energy delivery element to make contact with the epithelium.

32. The apparatus of claim 31, wherein the RF electrode is configured to have a width of about 0.75 cm to about 1.25 cm.

33. The apparatus of claim 31, wherein the RF electrode is configured to have a length of about 1 cm to about 3 cm.

34. The apparatus of claim 31, wherein the RF electrode is configured to have a radial curvature with respect to the longitudinal axis of the elongate shaft of up to 30 degrees.

35. The apparatus of claim 31, wherein the RF electrode curves radially with respect to the longitudinal axis at an arc of about 30 degrees.

36. The apparatus of claim 31, wherein the narrow portion is proximal to the energy delivery element.

37. The apparatus of claim 31, further comprising a cooling system within the elongate shaft configured to cool the energy delivery element.

38. The apparatus of claim 37, wherein the cooling system comprises cooling fluid and at least one nozzle, the nozzle configured to spray the cooling fluid on the energy delivery element.

39. The apparatus of claim 31, further comprising at least one thermister located in close proximity to the RF electrode.

40. The apparatus of claim 31, further comprising a programmable memory chip.

41. The apparatus of claim 31, further comprising a dielectric on an exterior of the energy delivery element.

42. The apparatus of claim 31, wherein the RF electrode has a width of between about 0.7 cm and 1.3 cm and a length of between about 1 to 4 cm.

43. An apparatus for remodeling a therapeutic zone within a target tissue, the target tissue comprising tissue underlying a mucosal epithelium of female genital tissue, the apparatus comprising:
    a treatment tip configured to releasably couple and decouple to a hand piece, the treatment tip comprising:
    an elongate shaft comprising a longitudinal axis, a proximal end, a distal end having a distal portion, and a narrow portion extending between the proximal end and the distal end, wherein the narrow portion narrows inwardly toward the longitudinal axis of the elongate shaft on a side of the elongate shaft, and
    a side-facing energy delivery element comprising an RF electrode on the elongate shaft and proximal to the distal end of the elongate shaft, the side-facing energy delivery element being disposed only along the same side of the elongate shaft as the narrow portion, wherein the RF electrode is curvilinear such that it curves radially with respect to the longitudinal axis while extending in parallel with the longitudinal axis, wherein the energy delivery element projects forward from the narrow portion on only a single side of the elongate shaft, and wherein the distal portion has a first surface and the narrow portion has a second surface, wherein the energy delivery element is only disposed on the first surface, wherein the first surface is substantially parallel to the second surface, and wherein the first surface is in a different plane than the second surface allowing for the energy delivery element to contact the epithelium.

44. The apparatus of claim 43, wherein the RF electrode is configured to be substantially parallel to the longitudinal axis of the elongate shaft and has a length of between about 1 to 4 cm.

45. The apparatus of claim 43, wherein the RF electrode is configured to have a width of about 0.75 cm to about 1.25 cm.

46. The apparatus of claim 43, wherein the RF electrode is configured to have a length of about 1 cm to about 3 cm.

47. The apparatus of claim 43, wherein the RF electrode curves radially with respect to the longitudinal axis at an arc of about 30 degrees.

48. The apparatus of claim 43, wherein the narrow portion is proximal to the energy delivery element.

49. The apparatus of claim 43, further comprising a cooling system within the elongate shaft configured to cool the energy delivery element.

50. The apparatus of claim 49, wherein the cooling system comprises cooling fluid and at least one nozzle, the nozzle configured to spray the cooling fluid on the energy delivery element.

51. The apparatus of claim 43, wherein the RF electrode is a monopolar RF electrode.

52. The apparatus of claim 43, wherein the energy delivery element is one RF electrode of a bipolar electrode pair of the energy delivery element.

53. The apparatus of claim 43, further comprising at least one thermister located in close proximity to the energy delivery element.

54. The apparatus of claim 43, further comprising a programmable memory chip.

55. The apparatus of claim 43, further comprising the hand piece adapted to be held by an operator, wherein the treatment tip is configured to connect to a distal end of the hand piece.

56. The apparatus of claim 43, further comprising a connector portion at a proximal end of the treatment tip configured to removably connect the treatment tip to the hand piece.

57. The apparatus of claim 43, further comprising a dielectric on an exterior of the energy delivery element.

58. The apparatus of claim 43, wherein the RF electrode is configured to have a fixed radial curvature with respect to the longitudinal axis of the elongate shaft of up to 30 degrees.

* * * * *